US007015312B1

(12) United States Patent
Wang et al.

(10) Patent No.: US 7,015,312 B1
(45) Date of Patent: Mar. 21, 2006

(54) ANTIBODIES TO THE PROTEIN PRODUCT ENCODED BY ORF3 OF THE TRP-1 GENE AND COMPOSITIONS AND KITS THEREOF

(75) Inventors: Rong-Fu Wang, Bethesda, MD (US); Steven A. Rosenberg, Potomac, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/571,313

(22) Filed: May 16, 2000

Related U.S. Application Data

(62) Division of application No. 09/197,816, filed on Nov. 23, 1998, now Pat. No. 6,087,110, which is a division of application No. 08/599,602, filed on Feb. 9, 1996, now Pat. No. 5,840,839.

(51) Int. Cl.
C07K 16/00 (2006.01)
(52) U.S. Cl. .............................. 530/388.85; 530/387.1; 424/130.1; 424/156.1
(58) Field of Classification Search ............. 530/387.1, 530/387.3–388.1, 388.85, 389.1, 389.7; 424/130.1, 424/156.1
See application file for complete search history.

(56) References Cited

U.S. PATENT DOCUMENTS 5,874,560 A * 2/1999 Kawakami et al.

FOREIGN PATENT DOCUMENTS

| WO | WO 91/14775 | 10/1991 |
| WO | WO 94/03205 | 2/1994 |
| WO | WO 95/23814 | 9/1995 |

OTHER PUBLICATIONS

Lederman et al., Molecular Immunology 28:1171-81, 1991.*
Smilek et al PNAS 88:9633-37, 1991.*
Lin et al., Biochemistry 14:1959, 1975.*
Burgess et al., The Journal of Cell Biology 111:2129-38, 1990.*
Schwartz et al., PNAS 84:6408-11, 1987.*
Lazar et al., Molecular and Cellular Biology 8:1247-1252, 1988.*
Kawakami, Y. et al, Identification of the Immunodominant Peptides of the MART-1 Human Melanoma Antigen Recognized by the Majority of HLA-A2-restricted Tumor Infiltrating Lymphocytes, *The Journal of Experimental Medicine*, vol. 180, pp. 347-352, Jul. 1994.
Yokoyama et al, Molecular cloning and functional analysis of a cDNA coding for human DOPAchrome tautomerase/ tyrosinase-related protein-2, *Biochimica et Biophysica Acta*, 1217 (1994) 317-321.
Vijayasaradhi et al, The Melanoma Antigen gp75 is The Human Homologue Of The Mouse b (Brown) Locus Gene Product, *J. Exp. Med.*, vol. 171, Apr. 1990, pp. 1375-1380.
Cohen et al, Nucleotide sequence of the cDNA encoding human tyrosinase-related protein, *Nucleic Acids Research*, vol. 18, No. 9, May 11, 1990, pp. 2807-2808.
Bloom et al, Identification of Tyrosinase-related Protein 2 as a Tumor Rejection Antigen for the B16 Melanoma, *Journal of Experimental Medicine*, vol. 185, No. 3, pp. 453-459, Feb. 3, 1997.
Wang et al, Identification of TRP-2 as a Human Tumor Antigen Recognized by Cytotoxic T Lymphocytes, *The Journal of Experimental Medicine*, vol. 184, pp. 2207-2216, Dec. 1996.
Orlow et al, Changes in expression of putative antigens encoded by pigment genes in mouse melanomas at different stages of malignant progression, *Proc. Natl. Acad. Sci. USA*, vol. 92, pp. 10152-10156, Oct. 1995.
Hara et al, Implicating a Role for Immune Recognition of Self in Tumor Rejection: Passive Immunization against the Brown Locus Protein, *J. Exp. Med.*, vol. 182, Nov. 1995, pp. 1609-1614.
Quelle et al, Alternative Reading Frames of the INK4a Tumor Suppressor Gene Encode Two Unrelated Proteins Capable of Inducing Cell Cycle Arrest, *Cell*, vol. 83, Dec. 15, 1995, pp. 993-1000.
Malarkannan et al, A Rare Cryptic Translation Product Is Presented by $K^b$ Major Histocompatibility Complex Class I Molecule to Alloreactive T Cells, *J. Exp. Med.*, vol. 182, Dec. 1995, pp. 1739-1750.
Wang et al, Identification of a Gene Encoding a Melanoma Tumor Antigen Recognized by HLA-A31-restricted Tomor-infiltrating Lymphocytes, *The Journal of Experimental Medicine*, vol. 181, Feb. 1995, pp. 799-804.
Wang et al, Human tumor antigens recognized by T lymphocytes: Implications for cancer therapy, *J. Leukocytes Biol.*, vol. 60, pp. 296-309, Sep. 1990.
Uenaka et al, Identification of a Unique Antigen Peptide pRL1 on BALB/c RL01 Leukemia Recognized by Cytotoxic T Lymphocytes and Its Relation to the Akt Oncogene, *J. Exp. Med.*, vol. 180, pp. 1599-1607, Nov. 1994.
Salgaller et al, Immunization against Epitopes in the Human Melanoma Antigen gp100 following Patient Immunization with Synthetic Peptides, *Cancer Research*, vol. 56:4749-4757, Oct. 1996.

(Continued)

Primary Examiner—Larry R. Helms
(74) Attorney, Agent, or Firm—Leydig, Voit & Mayer, Ltd.

(57) ABSTRACT

The present invention discloses that the normal melanogenic gene, gp75 gene, encodes a gene product, a 24 amino acid peptide of ORF3, which is processed to an antigenic cancer peptide recognized by T lymphocytes. The cancer peptide of the invention derived from ORF3 is recognized by cancer antigen specific T lymphocytes as a tumor rejection antigen. The products of this gene are promising candidates for immunotherapeutic strategies for the treatment and diagnosis of patients with cancer.

15 Claims, 8 Drawing Sheets

OTHER PUBLICATIONS

Wang et al, "Utilization of an alternative open reading frame of a normal gene in generating a novel human cancer antigen", *The Journal of Experimental Medicine*, vol. 183, No. 3, Mar. 1, 1996, pp. 1131-1140.

Bennett et al, Phenotypic rescue of mutant brown melanocytes by a retrovirus carrying a wild-type tyrosinase-related protein gene, Developement, vol. 110:471-475, 1990.

Murty et al. Assignment of the human TYRP (brown) locus to chromosome region 9p23 by nonradioactive in situ hybridzation, Genomics 13:227-229, 1992.

Cohen et al., *Nucleic Acids Res.*, 18(9), 2807-2808 (1990).

Miyoshi et al., *Hum. Mol. Genet.*, 1(4), 229-233 (1992).

Orlow et al., *Proc. Nat. Acad. USA*, 92, 10152-10156 (1995).

Townsend et al., *Nature*, 371, 662, (1994).

Wang et al., *J. Exp. Med.*, 181(2), 799-804 (1995).

Wang et al., *J. Exp. Med.*, 183(3), 1131-1140 (1996).

Wang et al., *J. Leukocyte Biol.*, 60(3), 296-309 (1996).

* cited by examiner

FIG. 2

```
SEQ ID NO:1 ┐
SEQ ID NO:2 ┬ATGAGTGCTCCTAAAACTCCTCTCTGGGCTGTATCTTTCTCCCCTGCTACTTTTTCAG 60
     ORF1    →M  S  A  P  K  L  L  S  L  G  C  I  F  F  P  L  L  L  F  Q

CAGGCCCGGGCTCAATTCCCAGACAGTGTGCCACTGTTGAGGCTTTGAGAAGTGGTATG 120
     ORF1     Q  A  R  A  Q  F  P  R  Q  C  A  T  V  E  A  L  R  S  G  M

TGTTGCCCAGACCTGTCCCCTGTGTCTGGGACCTGCTCTGGGACACAGACCGCTGTCATCATCA 180
     ORF1     C  C  P  D  L  S  P  V  S  G  P  G  T  D  R  C  G  S  S  S

GGGAGGGGCAGATGTGAGGCAGTGACTGCAGACTCCCGGCCCCACAGCCCTCAGTATCCC 240
SEQ ID NO:3 ┐ G  R  G  R  C  E  A  V  T  A  D  S  R  P  H  S  P  Q  Y  P       SEQ ID NO:5
     ORF1   →CATGATGGCAGAGATGATCGGGAGGTCTGCCCTTGCGCTTCTTCAATAGGACATGTCAC 300
     ORF1     H  D  G  R  D  D  R  E  V  W  P  L  R  F  F  N  R  T  C  H
     ORF2              SEQ ID NO:4 ───→M  I  G  R  S  G  P  C  A  S  S  I  G  H  V  T
                                                                         M  S  L      SEQ ID NO:6
            TGCAACGGCAATTTCTCAGGACACAACTGTGGACGTGCCGTCCTGGCTGGAGAGGAGCT 360
     ORF1     C  N  G  N  F  S  G  H  N  C  G  T  C  R  P  G  W  R  G  A
     ORF2     A  T  A  I  S  Q  D  T  T  V  G  R  A  V  L  A  G  E  E  L
     ORF3                                        Q  R  Q  F  L  R  T  Q  L  W  D  V  P  S  W  L  E  R  S  C

GCCCTGTGACCAGAGGGTTCTCATAGTCAGGAGGAATCTTCTGGACTTAAGTAAAGAAGAA 420
     ORF1     A  C  D  Q  R  V  L  I  V  R  R  N  L  L  D  D  L  S  K  E  E
     ORF2     P  V  T  R  G  F  S  STOP
     ORF3     L  STOP
                              ApaI
            AAGAACCACTTTGTCCGGGCCCTGGATATGGCAAAGCGCACAACTCACCCT...ATATGA 1584
     ORF1     K  N  H  F  V  R  A  L  D  M  A  K  R  T  T  H  P
```

ANTIBODIES TO THE PROTEIN PRODUCT ENCODED BY ORF3 OF THE TRP-1 GENE AND COMPOSITIONS AND KITS THEREOF

This application is a divisional of U.S. application No. 09/197,816, filed Nov. 23, 1998, now U.S. Pat. No. 6,087, 110, which is a divisional of U.S. application No. 08/599, 602, filed Feb. 9, 1996, now U.S. Pat. No. 5,840,839.

FIELD OF THE INVENTION

The present invention relates to the area of cancer diagnostics and therapeutics. More specifically, the invention relates to the isolation and purification of a novel cancer peptide and an alternative open reading frame DNA sequence encoding the cancer peptide. The invention further relates novel cancer peptide encoded by an alternative open reading frame DNA sequence from within the tyrosinase-related 1 (TRP 1) gene. The invention further relates to methods of detecting and diagnosing and treating cancer and precancer in an individual.

BACKGROUND OF THE INVENTION

The adoptive transfer of tumor infiltrating lymphocytes (TIL) can mediate tumor regression in patients with metastatic melanoma, suggesting that tumor rejection antigens recognized by T cells exist on these tumor cells. The availability of such T cells has made it possible to clone and sequence the genes that encode human melanoma antigens. The antigens identified so far from human melanoma can be divided into two classes based on their expression pattern. The antigens of the first class are encoded by genes that are expressed only in tumor and testis, but not other normal human tissues. MAGE1, MAGE3 and BAGE are examples of this class. The second class of antigens represents differentiation antigens encoded by genes that are expressed only in melanocytes, melanomas, and retina. MART-1/Melan-A, gp100 and tyrosine are examples of this class. All these antigens are nonmutated self proteins. Identification of the antigenic epitopes recognized by T-cells-derived from the corresponding gene products is important not only for understanding the mechanism of immune response to self antigens, but also for developing new, effective immunotherapeutic strategies with these antigens or synthetic peptides for the treatment of patients with cancer.

Previous studies showed that the infusion of TIL586 plus IL-2 into the autologous patient with melanoma resulted in the objective regression of metastases. More recently, the gene, tyrosinase-related protein 1 (TRP-1 or gp75) was cloned which encodes the tumor antigen recognized by TIL586 in association with HLA-A31. Interestingly, the gene product, gp75, was originally identified as an antigen recognized by IgG antibodies in the serum from a patient with metastatic melanoma. The gene was found to be expressed only in melanoma, normal melanocyte cell lines, and retina, but not in other normal tissues tested. Therefore, this gene is a member of the second class of antigens including MART-1/Melan-A, gp100 and tyrosinase.

In the art, it has been difficult to identify an epitope on a cancer cell which would be useful as an immunogen or vaccine to protect an individual from developing cancer. The present invention is the identification of a cancer peptide and the antigenic cancer epitope within the peptide encoded from an alternative open reading frame sequence within the TRP-1 gene which is specifically recognized by T cells. The cancer peptide of the invention is useful as an immunogen and vaccine to inhibit or prevent cancer in a mammal.

SUMMARY OF THE INVENTION

One object of the present invention is to provide a novel peptide and portions thereof recognized as a cancer antigen by T lymphocytes.

The cancer peptide of the present invention and the antigenic cancer epitope portion of the cancer peptide is encoded by an alternative open reading frame DNA sequence of a gene other than the open reading frame DNA sequence used to encode a normal protein or peptide from the same gene.

Another aspect of the invention is a tumor antigen encoded by an alternative open reading frame DNA sequence of a gene other than the open reading frame DNA sequence encoding a normal protein or peptide from the same gene.

Another aspect of the present invention is a pharmaceutical composition comprising a cancer peptide or antigenic cancer epitope thereof alone or in combination with one or more immunostimulatory molecules. The cancer peptide or antigenic cancer epitope thereof may be provided as an immunogen or as a vaccine for prevention or treatment of cancer. The pharmaceutical composition is useful in methods of treating or preventing cancer in a mammal. In the method of treatment, the pharmaceutical composition is administered to the mammal in an amount effective in preventing or inhibiting the cancer in the mammal.

Another object of the present invention is a method of generating cancer peptides and the antigenic cancer epitope within the peptide by translation of an alternative open reading frame DNA sequence from a gene other than the open reading frame DNA sequence encoding a normal protein from the same gene.

Yet another object of the invention is a method of detecting and identifying a cancer peptide gene product and portions thereof translated from an alternative open reading frame DNA sequence from a gene other than the gene product translated from the open reading frame DNA sequence encoding a normal protein or peptide.

A further aspect of the invention is the alternative open reading frame DNA or RNA sequence that encodes a cancer peptide or portion thereof and the use of the DNA or RNA sequence in methods of producing the cancer peptide or portions thereof. The invention further provides oligonucleotides of the alternative open readings frame DNA or RNA sequence for use as probes or primers.

The present invention further provides vectors comprising an alternative open reading frame DNA sequence encoding a cancer peptide or portions thereof alone or in combination with a second DNA sequence encoding at least one immunostimulatory molecule.

The invention also provides host cells transfected or transduced with a vector comprising an alternative open reading frame DNA sequence encoding a cancer peptide or portions thereof alone or in combination with a second DNA sequence encoding at least one immunostimulatory molecule.

The vectors and host cells may serve as vaccines in which expression of a cancer peptide or portion thereof results in the stimulation of cancer peptide specific T lymphocytes in a mammal immunized with the vaccine.

The invention provides a method of diagnosis cancer or precancer in a mammal by detection of a cancer peptide or portions thereof encoded by an alternative reading frame nucleic acid sequence of a gene other than the open reading frame nucleic acid sequence used to encode a normal protein from the same gene wherein the cancer peptide or portion thereof is recognized by T lymphocytes.

It is still another object of the invention to provide a method for diagnosing human preneoplastic and neoplastic cells and tissues. In accordance with the invention, the method comprises isolating cells, tissues or extracts thereof from a human and detecting the alternative open reading frame DNA sequence, RNA sequence or portion thereof encoding a cancer peptide or detecting the cancer peptide or portions thereof expressed by the alternative open reading frame DNA sequence or RNA sequence, wherein detection of/or increase in the alternative open reading frame DNA sequence, RNA sequence or expression product is indicative of preneoplasia and neoplasia.

Still another object of the invention is to provide a transgenic animal which has incorporated into its genome one or more copies of the alternative open reading frame DNA sequence encoding a cancer peptide or portion thereof. The incorporation of the alternative open reading frame DNA sequence results in overexpression or expression of multiple forms or variants of the cancer peptide. Such transgenic animals are useful for screening of therapeutic agents useful in treating cancer.

The invention also encompasses antisense oligonucleotides which specifically target and bind to the alternative open reading frame nucleic acid sequence and inhibit the expression of the cancer peptide without adversely affecting the expression of the normal protein from the same gene.

Still another aspect of the invention are monoclonal and polyclonal antibodies reactive with the cancer peptide and antigenic cancer epitope thereof, for use in diagnostic and detection assays. The monoclonal and polyclonal antibodies may be provided in the form of a kit alone, or along with other reagents commonly used in diagnostic and detection assays.

BRIEF DESCRIPTION OF THE FIGURES

These and other objects, features, and many of the attendant advantages of the invention will be better understood upon a reading of the following detailed description when considered in connection with the accompanying drawings wherein:

FIG. 1A shows the full length cDNA which comprises the 1584 bp open reading frame of gp75 is shown. Nucleotides are numbered from the start codon which translates into a protein consisting of a leader sequence and the mature gp75. pcDNA776 is a partial cDNA of gp75 which lacks the first 246 nucleotide coding region and was isolated from a cDNA library using an assay based on its ability to stimulate GM-CSF secretion by TIL586 when co-transfecting COS-7 along with the HLA-A31 gene. A series of deletion constructs and PCR DNA fragments were made. pD776A is a derivative of pcDNA776 after digestion with the ApaI restriction enzyme.

FIG. 1B shows GM-CSF release by TIL586. GM-CSF secretion by TIL586 was measured after co-cultured with COS-7 co-transfected with the DNA fragments shown in FIG. 1A and the HLA-A31 gene. Control stimulator cells include 586mel, 397mel/A31+, COS-7 alone, and COS-7 transfected either the HLA-A31 or the pcDNA776 cDNA.

FIG. 2 shows the nucleotide, amino acid sequence and open reading frames of the gp75 gene. The partial nucleotide and amino acid sequences of the first 157 amino acids was shown from the start codon for translation of ORF1 (gp75). The DNA fragment that conferred the ability to stimulate GM-CSF release from TIL586 is underlined. Two putative start codons, ATG (254–256) and ATG (294–296), are in bold and may result in the translation of ORF2 and ORF3, respectively. The peptide sequence recognized by TIL586 from ORF3 is in bold and underlined.

FIG. 3A shows the location and length of PCR fragments amplified by PCR. DNA fragments were obtained by PCR amplification and were then cloned into the pCR3 expression vector. Substitution of ATG at positions 294–296 with ATC was made as described in Material and Methods.

FIG. 3B shows the testing of DNA fragments and mutation constructs to stimulate cytokine release from TIL586. GM-CSF release assay was done as in FIG. 1.

FIG. 4A shows GM-CSF release by the HLA-A31 restricted TIL586 when co-incubated with various stimulators. Transfection and cytokine assays were performed as FIG. 1A and b. 586mel and 397mel were included as positive and negative controls for the reactivity of TIL586. The ORF3P peptide was incubated with 586EBV (A31+) and T2 (non-A31) cells at a concentration of 1 μg/ml for 90 min. Stimulation of GM-CSF secretion by TIL586 significantly increased when co-incubated with autologous 586EBV and allogeneic 1510EBV (A31+) cells pulsed with peptide ORF3P, but not when co-incubated with either 586EBV alone or T2 (non-A31) cells loaded with the ORF3P peptide.

FIG. 4B shows cytotoxic lysis of the target cells by TIL586. 586mel (—■—) and 397mel (—□—) were used as positive and negative controls, respectively. 586EBV B cells were incubated with ORF3P (pep) (—▲—), with an irrelevant peptide (ipep) (—●—) without peptide (—△—) and T2 cells pulsed with ORF3P (—○—) as marked. After incubation, TIL586 was added and mixed with the target cells. Cytolytic activity of TIL586 was measured in a 4 h chromium release assay.

FIG. 4C shows titration of the peptide concentration to sensitize the target cells for lysis by TIL586. 586EBV cells were separately incubated with serial dilutions of ORF3P (pep) (—▲—) or irrelevant peptides (ipep) (—●—) and T2 cells with the ORF3P (peptide (—○—) for 90 min. The cytolytic activity of TIL586 was evaluated in a 4h $^{51}$Cr release assay at an effector: target (E:T) ratio of 40:1.

FIG. 5A shows 586mel cells were labeled with chromium for 90 min as a "hot" target. 586EBV cells pulsed with ORF3P (—▲—), with irrelevant peptide (—△—) and T2 cells loaded with ORF3P (—□—) were used as "cold" target cells. After washing, "hot" and "cold" target cells were counted again and mixed at the "cold"/"hot" ratio of 1:1, 5:1, 10:1, and 20:1. TIL586 was added at an effector; "hot" target (E:T) ratio of 20:1. Chromium release was measured after 4 h incubation.

FIG. 5B shows lysis of $^{51}$Cr-labeled 624mel ("hot" target) by TIL1200 which recognized gp100 was not inhibited by 586EBV cells pulsed with ORF3P (—▲—) compared to 586EBV cells pulsed with an irrelevant peptide (—△—).

Figure 1A:
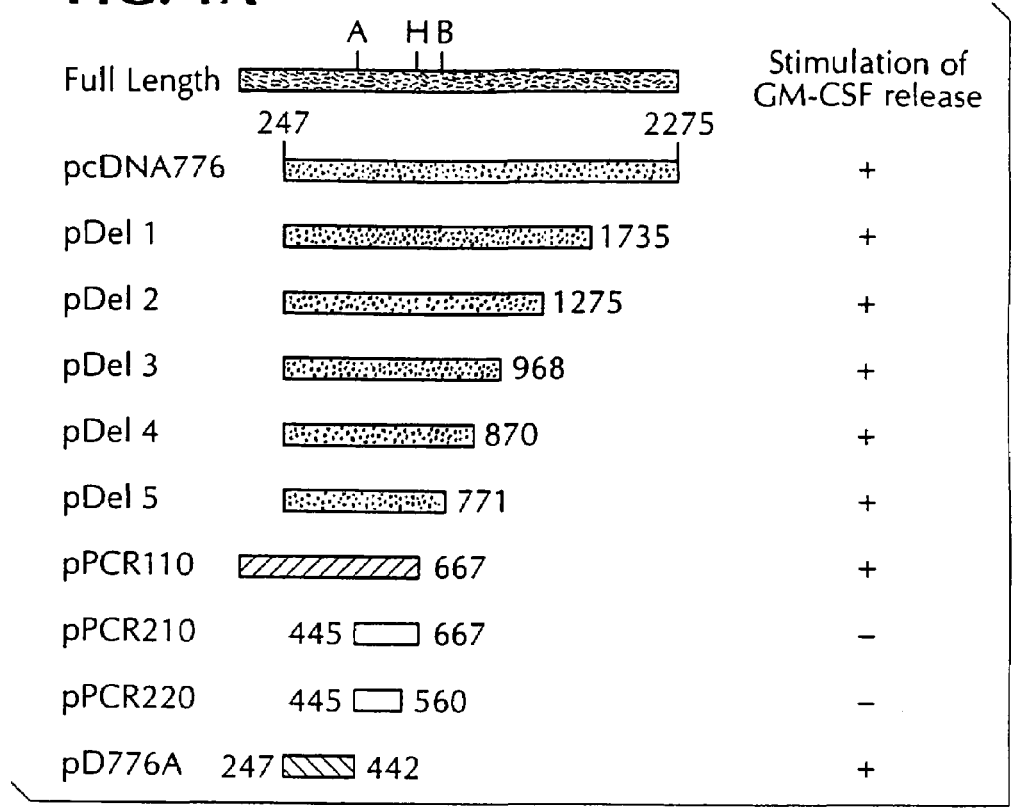
FIGS. 1A and 1B show the location of the gp75 nucleotide sequence coding for the antigenic peptides recognized by TIL586.

"Cold" and "hot" target cells were mixed at the indicated ratios. TIL1200 was added at an effector: hot target (E:T) ratio of 30:1. Cytolytic activity of TIL1200 was evaluated in a 4-h $^{51}$Cr release assay.

FIGS. 6A–6D show recognition of the antigenic peptide T cell clones from the TIL586 cell line. T cell clones were generated from the TIL586 cell line. 586EBV B cells were pulsed with the ORF3P peptide or irrelevant peptide. T cell clone or TIL586 cells were added and coincubated. For 586 mel, 397 mel/A31$^+$ tumors and melanocyte NHEM680 cells, 1×10$^5$ cells per well were incubated with 1×10$^5$ cells clones, TIL586-C1 (FIG. 6A), TIL586-C4 (FIG. 6B) and TIL586-C6 (FIG. 6C) or TIL586 (FIG. 6D) for 18–24 h, respectively. GM-CSF assay was performed as described in FIG. 1B.

DETAILED DESCRIPTION OF THE INVENTION

The present invention encompasses cancer peptides and portions or derivatives thereof which are immunologically recognized by T lymphocytes of the immune system. The present invention further encompasses the antigenic cancer epitope(s) which are contained in the cancer peptides. The antigenic cancer epitope specifically causes a cellular mediated immune response by interaction with T cells of the immune system. This interaction between the antigenic cancer epitope and the T cells causes the T cells to respond against, and prevent, eliminate or reduce the cancer in a mammal, including humans.

The cancer peptides and the antigenic cancer epitope contained within the cancer peptides of the present invention are distinguished from normal protein or peptides in that the cancer peptides are encoded by an alternative open reading frame of a gene other than the open reading frame that encodes the normal protein or peptide within the gene. The cancer peptide and portions thereof are characteristically absent from or present in very low levels from normal cells and are present in high levels from pre-cancer and cancer cells. Expression of the cancer peptide at high levels correlates with transformation of normal cells to a pre-cancer or cancer cell.

The cancer peptides of the present invention form part of, or are derived from, cancers including but not limited to primary or metastatic melanoma, thymoma, lymphoma, sarcoma, lung cancer, liver cancer, non-Hodgkin's lymphoma, Hodgkins lymphoma, leukemias, uterine cancer, cervical cancer, bladder cancer, kidney cancer and adenocarcinomas such as breast cancer, prostate cancer, ovarian cancer, pancreatic cancer, and the like.

The term melanoma includes, but is not limited to, melanomas, metastatic melanomas, melanomas derived from either melanocytes or melanocytes or melanocyte related nevus cells, melanocarcinomas, melanoepitheliomas, melanosarcomas, melanoma in situ, superifical spreading melanoma, nodular melanoma, lentigo maligna melanoma, acral lentiginous melanoma, invasive melanoma or familial atypical mole and melanoma (FAM-M) syndrome.

Of particular interest are cancer peptides, fragments or derivatives thereof recognized by autologous CTL in patients with cancer, in particular melanoma. Of further interest are cancer peptides, fragments or derivatives thereof recognized by MHC restricted CTL, in particular MHC class I restricted CTLs.

The cancer peptides of the present invention arise from expression of an alternative open reading frame DNA sequence from a normal gene. Rather than the normal gene product being expressed, a cancer peptide is expressed which is capable of being immunologically recognized by T lymphocytes in an MHC restricted manner. The MHC restricted T lymphocytes are useful in identifying the alternative open reading frame gene product associated with cancer and pre-cancer.

Of particular interest are cancer peptides which are associated with TRP-1 (gp 75); the protein, p19$^{ARF}$, which arises from an alternative reading frame of the mouse tumor suppressor INK4a gene (Quelle, D. E. et al. *Cell* Vol. 83, pp. 993–1000, 1995); the antigenic octapeptide SVVEFSSL SEQ ID NO:46, i.e. JAL8, an allogeneic peptide recognized by bm1 and anti-B6 all reactive bm1BZ19.4 T-cells (Malarkannan, S. et al. *J. Exp. Med.* Vol. 182, pp. 1739–1750, 1995) and the like.

In one embodiment, a cancer peptide, fragment or derivative thereof of the present invention comprises antigenic cancer epitope immunologically recognized by tumor infiltrating lymphocytes (TIL) derived from a cancer tumor of a mammal. Of particular interest are antigenic cancer epitopes recognized by cancer antigen specific cytotoxic T cells (CD 8$^+$).

In one embodiment of the present invention the cancer peptide comprises about 24 amino acids and is expressed by the alternative open reading frame 3 DNA sequence from the same gene that encodes tyrosinase-related protein as depicted in FIG. 2 or from homologs or variants thereof.

In one embodiment, the cancer peptide of the present invention comprises the amino acid sequence: MXaaLQRQ-FLRTQLWDVPSWLERSCL, (SEQ ID NO: 7) and fragments, or derivatives thereof, wherein Xaa=Ser or Ala. Also encompassed in the ambit of the invention are cancer peptides or portions thereof that share partial sequence homology with SEQ ID NO: 6. By partial amino acid sequence homology is meant a peptide having at least 85% sequence homology with SEQ. ID NO: 6, preferably at least 95% sequence homology or greater and has the biological function of stimulating cancer antigen specific T lymphocytes.

In an embodiment of the present invention the cancer peptide may be represented by the formula:

Met Xaa Leu Gln Arg Gln Phe Leu Arg (SEQ ID NO: 8) and fragments and derivatives thereof wherein Xaa=Ser or Ala.

In another embodiment the cancer peptide of the present invention comprises the amino acid sequence:

MSLQRQFLR (SEQ. ID NO: 9) and fragments and derivatives thereof.

The cancer peptides and their antigenic cancer epitopes may be purified and isolated from natural sources such as from primary clinical isolates, cell lines and the like. The cancer peptide and portions thereof are at least 90% pure, preferably at least 95% pure and as pure as 100%. The cancer peptides and their antigenic epitopes may also be obtained by chemical synthesis or by recombinant DNA techniques known in the arts. Techniques for chemical synthesis are described in J. M. Steward and J. D. Young, "Solid Phase Peptide Synthesis", W. H. Freeman & Co., San Francisco, 1969; M. Bodansky et al "Peptide Synthesis", John Wiley & Sons, Second Edition, 1976, and J. Meienhofer, "Hormonal Proteins and Peptides", Vol. 2, p. 46, Academic Press, New York, 1983 and E. Schroder and Kubke, "The Peptides", Vol. 1, Academic Press, New York, 1965.

The cancer peptides and their antigenic cancer epitopes may be formulated with pharmaceutically acceptable carriers into pharmaceutical compositions by methods known in the art. The composition is useful as a vaccine to prevent or treat cancer. The composition may further comprise at least one immunostimulatory molecule. Immunostimulatory molecules to be used in conjunction with the cancer peptide or portion thereof for stimulating antigen specific T cell responses include but are not limited to one or more histocompatibility complex (MHC) molecules, such as class I and class II molecules, preferably a class I molecule. The composition may further comprise other stimulator molecules including B7.1, B7.2, ICAM-1, ICAM-2, LFA-1, LFA-3, CD72 and the like, and cytokines which include but are not limited to IL-1 through IL-15, TNFα, IFNγ, RNATES, G-CSF, M-CSF, IFNα, CTAP III, ENA-78, GRO, I-309, PF-4, IP-10, LD-78, MGSA, MIP-1α, MIP-1β, or combination thereof, and the like for immunopotentiation.

The stimulatory molecule may be provided as a physically separate entity or it may be provided in the membrane of an antigen presenting cell such as B-cell, macrophage or dendritic cell, in the membrane of a liposome, or expressed on the surface of a transduced or transfected cell. DNA sequences of MHC immunostimulatory molecules are available from GenBank and the like.

targeting agents may be hormones, cytokines, cellular receptors and the like. The cancer peptide and portions thereof may be prepared in the form of a kit, alone or in combination with other reagents.

Another aspect of the invention is a vaccine useful in inducing tumor specific cell-mediated immunity against cancer.

Approaches to cancer immunotherapy can be divided into active or passive categories. Active immunotherapy involves the direct immunization of cancer patients with cancer antigens in an attempt to boost immune responses against the tumor. Passive immunotherapy refers to the administration of immune reagents, such as immune cells or antibodies with antitumor reactivity with the goal of directly mediating antitumor responses.

Most prior attempts at active immunotherapy utilized either intact cancer cells or cancer cell extracts with the expectation that these materials contained tumor antigens in an amount and form capable of stimulating immune responses. The molecular identification of cancer antigens however, has open new possibilities for developing immunotherapies for the treatment of human cancer. A summary of some of these approaches is presented in Table 1.

TABLE 1

Cancer Therapies Based on the Molecular Identification of Cancer Antigens

1. Active immunotherapy with:
   a. Immunodominant peptides
      1) alone
      2) combined with adjuvants
      3) linked to helper peptides, lipids or liposomes
      4) pulsed onto antigen presenting cells
   b. Immunodominant peptides with amino acids substitutions to increase binding to MHC molecules
   c. Proteins alone or combined with adjuvants
   d. "Naked" DNA encoding cancer antigens
      1) "gene gun" for intradermal injection
      2) intramuscular injection
      3) linked to lipids
   e. Recombinant viruses such as vaccinia, fowlpox or adenovirus encoding
      1) cancer antigens alone
      2) cancer antigens plus genes encoding cytokines, costimulatory molecules, or other genes to enhance the immune response
   f. Recombinant bacteria such as BCG, *Salmonella* or *Listeria* encoding cancer antigens alone or in combination with immunostimulatory molecules
2. Active immunotherapy (above) followed by the administration of immunostimulatory cytokines.
   1. IL-2
   2. IL-6
   3. IL-10
   4. IL-12
   5. IL-15, and the like.
3. Passive immunotherapy with anti-tumor lymphocytes raised by in vitro sensitization of TIL or PBL to
   1. immunodominant peptides pulsed onto antigen presenting cells (raise CD8 cells)
   2. antigenic proteins coincubated with antigen presenting cells (exogenous antigen presenting pathway to raise CD4 cells).

The cancer peptides and their antigenic cancer epitopes are useful in methods of preventing or treating cancer and useful in diagnostic assay for detecting cancer or precancer in a mammal, including humans. The cancer peptides or portions thereof may be in the form of a derivative in which other constituents are attached thereto such as radiolabels, biotin, fluorescein. A targeting agent may also be attached to the cancer peptides or portions thereof that allow for specific targeting to a specific organ, tumor or cell types. Such The insertion of the gene encoding cancer antigens into high efficiency expression systems such as *E. coli,* yeast or baculovirus and the like provides the opportunity to obtain large amounts of purified tumor antigen for use in immunization. Alternatively, the immunodominant peptides from these tumor antigens could readily be synthesized in vitro and purified in large amounts for immunization alone or in a form intended to improve their immunogenicity such as in combination with adjuvant, linkage to lipids/liposomes or helper peptides, or pulsed onto antigen presenting cells. Modification of individual amino acids of the immunodominant peptides to improve binding efficiency to MHC antigens can potentially increase immunogenicity compared to the native peptide.

Recent techniques utilizing "naked" DNA injected directly into muscle or into the skin have been shown to raise both cellular and humoral immune reactions to encoded antigens (Cooney, E. L., A. C. Collier, P. D. Greenberg, R. W. Coombs, J. Zarling, D. E. Arditti, M. C. Hoffman, S. L. Hu and L. Correy, 1991, *Lancet* 337:567; Wolff, J. A., R. W. Malone, P. Williams, W. Chong, G. Acsadi, A. Jani, and P. L. Felgner, 1990, *Science* 247:1465; Davis, H. L. R. G. Whalen, and B. A. Demeniex, 1993, *Hum. Gene Ther.* 4:151; Yang, N. S., J. Burkholder, B. Roberts, B. Martinelli, and D. McCabe, 1990, *Proc. Natl. Acad. Sci. USA* 87:9568; Williams, R. S. S. A. Johnston, M. Riedy, M. J. DeVit, S. G. McElligott, and J. C. Sanford, 1991, *Proc. Natl. Acad. Sci. USA* 88:2726; Fynan, E. R., Webster, D. H. Fuller, J. R. Haynes, J. C. Santoro, and H. L. Robinson, 1995, *Proc. Natl. Acad. Sci. USA* 90:11478; Eisenbraum, M. D., D. H. Fuller, and J. R. Haynes, 1993, *DNA and Cell Bio.* 12:791; Fuller. D. H. and J. R. Haynes, 1994, *AIDS Res. Hum. Retrovir.* 10(11):1433; Acsadi, G., G. Dickson, D. R. Love, A. Jani, F. S. Walsh, A. Gurusinghe, J. A. Wolff, and K. E. Davies, 1991, *Nature* 352:815). Techniques using nonviable DNA vectors have the advantage of ease of preparation and safety of administration. The alternative nucleic acid sequence of the present invention is useful as an immunogen and as a DNA vaccine against cancer. The alternative open reading frame nucleic acid sequence of the present invention may be administered using a gene gun in amounts to elicite a cellular response against a cancer cell. Nonogram quantities are useful for such purposes.

An effective form of immunization involves the incorporation of genes encoding immunogenic molecules into recombinant bacteria such as BCG, Salmonella or Listeria or into recombinant viruses such as vaccinea, fowlpox or adenovirus and the like. The genes encoding cancer antigens can be expressed either alone or in combination with genes encoding immunostimulatory molecules or other genes which can enhance the immune response following infection. Studies with model tumor antigens in murine models have shown that incorporation of the gene for interleukin-2 (IL-2) or B7.1 can increase the immunogenicity of model tumor antigens and even mediate the regression of established lung metastases bearing these antigens and even mediate the regression of established lung metastases bearing these antigens. Active immunotherapy followed by the exogenous administration of immunostimulatory cytokines such as IL-2, IL-6, IL-10, IL-12, or IL-15 may be used to improve immune responses.

Passive immunotherapy with genetically modified immune cells (commonly referred to as adoptive immunotherapy) capable of recognizing human tumor antigens is effective in mediating the regression of cancer in selected patients with metastatic several weeks to months may be preferable. Subsequent doses may be administered as indicated.

In a method of treatment, a vaccine comprising the cancer peptide or portion thereof is administered to a mammal in an amount effective to prevent cancer in the mammals. Of particular interest is a vaccine comprising the cancer peptide or portion thereof encoded by ORF3 of the TRP-1 gene for prevention of melanoma.

In a method of reducing tumor burden in animals having tumors the method comprises administration of an effective amount of a antigenic cancer epitope at a site of tumor burden, said amount is effective to reduce the size of the tumor at the site.

In another method of treatment, autologous cytotoxic lymphocytes or tumor infiltrating lymphocytes may be obtained from a patient with cancer. The lymphocytes are grown in culture and cancer antigen specific lymphocytes expanded by culturing in the presence of specific cancer peptides or antigenic cancer epitopes alone or in combination with at least one immunostimulatory molecule with cytokines. The antigen specific lymphocytes are then infused back into the patient in an amount effective to reduce or eliminate the tumors in the patient.

After immunization the efficacy of the vaccine can be assessed by production of immune cells that recognize the cancer antigen, as assessed by specific lytic activity, specific cytokine production, tumor regression or combination of these. If the mammal to be immunized is already afflicted with cancer or metastasis cancer the vaccine can be administered in conjunction with other therapeutic treatments such as immunomodulators, for example, IL-2, IL-6, IL-10, IL-12, IL-15, interferon, tumor necrosis factor and the like, chemotherapeutic drugs such as cisplatinum, antiviral such as gancyclovir, amphotericin B, antibiotics and the like.

Another aspect of the invention is an alternative open reading frame DNA sequence of a gene other than the open reading frame DNA sequence encoding a normal protein or peptide wherein the alternative open reading frame DNA sequence encodes cancer peptides and portions thereof which are immunologically recognized by T cells of the immune system.

Alternative open reading frame DNA sequence include but are not limited to DNA sequences from the TRP-1 gene, the TRP-2 gene, the INK4a gene and the like.

Of interest are alternative open reading frame DNA sequence from a melanogenic gene. Melanogenic genes include but are not limited to genes encoding MART-1/Melan A, tyrosinase, gp 100, gp 75 (TRP-1), TRP-2 (Halahan, R. et al 1993 *J. Invest. Dermatol.* 100 (Suppl.): 176S–185S), and the like.

One embodiment of the invention is an alternative open reading frame DNA sequence or portion thereof encoding a cancer peptide from within the gene sequence that encodes tyrosinase-related protein. The gene sequence for TRP1 has been disclosed through the EMBL data bank under accession number X51455 as described by Vijayasaradhi, S. et al (1990, *J. Exp. Med.* 171:1375–80) and EMBL accession number X51420 as described by Cohen, T. et al 1990 *Nucleic Acids Research,* Vol. 18:2807.

In one embodiment, the alternative open reading frame DNA sequence comprises ORF3 depicted in FIG. 2 having SEQ. ID NO.: 5, portions thereof and functionally equivalent sequence variant thereof that encode a cancer peptide or portions thereof recognized by cancer antigen specific T lymphocytes including tumor infiltrating lymphocytes. Also encompassed by the present invention are nucleic acid sequences complementary, as well as anticomplementary to ORF3 depicted in FIG. 2.

In another embodiment, the alternative open reading frame DNA sequence comprises:

ATGTCACTGCAACGGCAATTTCTCAGG (SEQ ID NO: 10).

Due to degeneracy in the generic code, variations in the DNA sequence will result in translation of an equivalent cancer peptide. As a result, substitutions are included in the ambit of the invention as long as the substitution results in expression of a cancer peptide that is recognized by cancer antigen MHC-restricted T cells. One substitution encompassed in the present invention is the substitution of TCA encoding Ser for GCT, GCC, GCA or GCG encoding Ala. Homologs from other mammalian species is included within the ambit of the invention.

All or part of the alternative open reading frame DNA sequence may be used as probes to identify and isolate the homologs of the cancer peptide in other mammalian species. In one embodiment, a murine cDNA sequence is used to screen a mammalian cDNA library for a human homolog nucleic acid sequence. Positive clones are selected and sequenced. Examples of tissue sources from which the cDNA library can be synthesized include but are not limited to dermis, epidermis, solid tumors, melanomas, melanocytes, and the like. One skilled in the art will understand the appropriate hybridization conditions to be used to detect the homologs. Conventional methods for nucleic acid hybridization construction of libraries and cloning techniques are described in Sambrook et al, (eds) (1989) in "Molecular Cloning. A Laboratory Manual" Cold Spring Harbor Press, Plainview, N.Y. and Ausubel et al (eds) in "Current Protocols in Molecular Biology" (1987), John Wiley and Sons, New York, N.Y.

Another aspect of the invention are nucleic acid probes for the detection and quantification of RNA that transcribes the cancer peptides in biologic samples isolated from a mammal with cancer. Alterations in the level of RNA relative to a control RNA sample is useful in diagnosis and prognosis of the disease in the mammal. In one embodiment mRNA is derived from tissue of a patient suspected of having cancer or precancer and compared with mRNA derived from a healthy control subject. A quantitative and/or qualitative increase of the alternative open reading frame mRNA encoding a cancer peptide in the patient, as compared to the control, is indicative of cancer or precancer in the patient. The mRNA may be detected using oligonucleotides probes.

Combinations of oligonucleotides pairs based on the sequence encoding the cancer peptide or portions thereof may be used as PCR primers to detect mRNA in biological samples using the reverse transcriptase polymerase chain reaction (RT-PCR) process for amplifying selected RNA sequences. The present invention also encompasses in situ PCR and in situ RT-PCR for detection of DNA and RNA encoding the cancer peptides or portions thereof. The techniques is preferred when the copy number of a target nucleic acid is very low, or when different forms of nucleic acids must be distinguished. The method is especially useful in detecting and differentiating precancer and cancer cells from normal cells.

The present invention includes a method of identifying an antigenic cancer epitope reactive with antigen specific T cells comprising the generation of nucleic acid deletion fragments from a gene. The deletion fragments are placed in an appropriate vector which in turn are transfected or transduced into a host cell for the expression of the nucleic acid product. Optionally, the host cell may also express an immunostimulatory molecule. Cancer antigen specific T-cell responses are determined in the presence of the host cell expressing the deletion product.

In the case where the host cell expresses only the deletion product, a immunostimulatory molecule may be provided by an antigen presenting cell such as a B cell, macrophage, dendritic cell and the like or by a cell transfected with a stimulatory molecule. In one embodiment, the immunostimulatory molecule is a MHC class I molecule.

By mapping using this approach, the alternative open reading frame DNA sequence encoding the cancer peptide or the antigenic cancer epitope is determined.

An alternative method of identifying the cancer antigen and the antigenic cancer epitope is by generating synthetic peptides, pulsing antigen presenting cells with the synthetic peptides and adding the peptide pulsed antigen presenting cells with antigen specific T cells and measuring the antigen specific response to T cells in the presence of the peptide pulsed antigen presenting cells. The synthetic peptides that result in antigen specific T cell responses contains the antigenic cancer epitope of the present invention.

The present invention also encompassed vector comprising the alternative open reading frame DNA sequence encoding cancer peptides or the antigenic cancer epitope. Optionally the vector may also comprise a DNA sequence encoding at least one immunostimulatory molecule.

Eukaryotic expression vectors include but are not limited to retroviral vectors, vaccinia virus vectors, adenovirus vectors, herpes virus vectors, fowlpox virus vectors, baculovirus vectors, human papillomavirus vectors, equine encephalitis vectors, influenza virus vectors and the like.

The present invention encompasses novel recombinant virus expressing a cancer peptide or portion thereof encoded by an alternative open reading frame nucleic acid sequence of a gene other than the open reading frame nucleic acid sequence used to encode a normal protein or peptide from the same gene. The recombinant virus may also express at least one immunostimulatory molecule. The recombinant virus is capable of eliciting or upregulating a cell-mediate immune response in a mammal for the purpose of preventing or treating cancer in the mammal, particularly humans.

The recombinant virus has incorporated into its genome or portion thereof a nucleic acid sequence encoding a cancer peptide, portion thereof, or antigenic cancer epitope, alone, or in combination with one or more genes encoding an immunostimulatory molecule. A host cell infected with the recombinant virus expresses the cancer peptide, portion thereof, or antigenic cancer epitope, alone or in combination with at least one immunostimulatory molecule.

Methods for constructing and expressing exogenous gene products from recombinant vaccinia virus vectors are disclosed by Perkus et al Science 229:981–984, 1985, Kaufman et al Int. J. Cancer 48:900–907, 1991, Moss Science 252: 1662, 1991, Smith and Moos BioTechniques Nov/Dec. p. 306–312, 1984, and U.S. Pat. No. 4,738,836. Sutter and Moss (Proc. Nat'l Acad. Sci. U.S.A. 89:10847–10851, 1992) and Sutter et al (Virology 1994) disclose the construction and use a sa vector, the non-replicating recombinant Ankara virus (MVA, modified vaccinia Ankara) which may be used as a viral vector in the present invention. Baxby and Paoletti (Vaccine 10:8–9, 1992) disclose the construction and use as a vector, a non-replicating proxvirus, including canarypox virus, fowlpox virus and other avian species for use as a viral vector in the present invention.

The vectors of the present invention may be placed in an appropriate host cell for the expression of the cancer peptide or antigenic cancer epitope. Eukaryotic host cell lines include, but are not limited to COS cells, CHO cells, Hela cells, NIH/3T3 cells, insect cells, antigen presenting cells such as dendritic cells and the like. Optionally the host cell may also express a stimulatory molecule. In the case where the host cells express both the cancer peptide or antigenic cancer epitope in combination with at least one MHC molecule, it is preferable that a eukaryotic expression system be used to allow for proper glycosylation. The expression of both the cancer antigen and the immunostimulatory molecule by the host cell provides the necessary MHC restricted peptide to specific T cells and the appropriate signal to the T cell to aid in antigen recognition and proliferation or clonal expansion of antigen specific T cells. The overall result is an upregulation of the immune system. The upregulation of the immune response is manifest by an increase in cancer antigen specific cytotoxic lymphocytes which are able to kill or inhibit the growth of cancer or precancer cells.

The DNA may be inserted into the host cell by transfection, transduction, liposomes and the like by methods known in the art. (Sambrook et al. 1989, in: "Molecular Cloning A Laboratory Manual", Cold Spring Harbor press, Plainview, N.Y.). For liposomes, cationic lipids are preferred for example, polycationic lipid, dimyristyloxypropyl-3-dimethyl-hydroxyethyl ammonium (DMRIE) complexed with the neutral phospholipid dioleoyl phosphatidyl-ethanolamine (DOPE) as disclosed by Nabel, E. G. et al., 1992, $Hum.$ $Gene. Ther.$ 3:367–275; Nabel, G. J. et al., 1992, $Hum. Gene$ $Ther.$ 3:649–656; Stewart, M. J. et al 1992 $Hum. Gene Ther.$ 3:399–410; Nabel, G. J. et al. 1993 $Proc. Natl. Acad. Sci.$ USA 90:13307–11311; and Harrison, G. S. et al 1995 $Bio$ $Techniques$ 19:816–823.

The recombinant cancer protein or antigenic cancer epitope expressed by the host cells may be purified from cell lysates or cell supernatants by standard protein purification procedures known in the art. These include but are not limited to molecular sieve chromatography, ion-exchange chromatography, isoelectric focusing, gel electrophoresis, affinity chromatography, HPLC, reverse phase HPLC and the like. (Ausubel et al., 1987, in $Current Protocols in$ $Molecular Biology$, John Wiley and Sons, New York, N.Y.). Immunoaffinity chromatography may also be used for purification using anti-cancer protein antibodies or antigen binding fragments thereof as described herein, as the immunoaffinity agent.

The recombinant virus may also be used as a therapeutic or vaccine. In such uses it is desirable to provide the recipient with a dosage of recombinant virus in the range of from about $10^5$ to about $10^{10}$ plaque forming units/mg mammal, although a lower or higher dose may be administered.

The recombinant viral vector may be introduced into a mammal either prior to any evidence of cancer such as melanoma or to mediate regression of the disease in a mammal afflicted with a cancer such as melanoma. Examples of methods for administering the viral vector into mammals include, but are not limited to, exposure of cells to the recombinant virus ex vivo, or injection of the recombinant virus into the affected tissue or intravenous, subcutaneous, intradermal, intramuscular and the like administration of the virus. Alternatively, the recombinant viral vector or combination of recombinant viral vectors may be administered locally by direct injection into the cancerous lesion or topical application in a suitable pharmaceutically acceptable carrier. The quantity of recombinant viral vector, carrying the nucleic acid sequence of interest is based on the titer of virus particles. A preferred range for immunization is about $10^5$ to $10^{10}$ virus particles per mammal, preferably a human.

Cancer antigen epitope of the present invention which is involved in tumor rejection is not limited to the ones specifically disclosed herein. Using the methods disclosed in the present invention other cancer antigen epitopes contained in alternative open reading frame products may be identified from other tumor associated antigens (Van der Bruggen, P. et al 1991 $Science$ 254:1643–47; Gaugler, B. et al. 1994 $J. Exp. Med.$ 179:921–30; Boel, P. et al 1995 $Immunity$, 2:167–75; Brichard, V. et al. 1993, $J Exp. Med.$ 178:489–95; Robbins, P. F. et al. 1994, $Cancer Research$ 54:3124–26; Kawakami, Y. et al 1994, $Proc. Natl. Acad. Sci.$ $U. S. A.$ 91:3515–19; Coulie, P. G. et al 1994 $J. Exp. Med.$ 180:35–42; Bakker, A. et al 1994, $J. Exp. Med.$ 179:1005–09) such as from MART-1/Melan A (Kawakami et al $J. Exp. Med.$ 180:347–352, 1994), MAGE-3 (Gaugler et al $J. Exp. Med.$ 179:921–930, 1994), gp 100 (Kawakami et al $Proc. Nat'l Acad. Sci. U.S.A.$ 91:6458–6462, 1994), tyrosinase (Brichard et al $J. Exp. Med.$ 178:489, 1993), TRP-2, CEA, CA-19-A, CA-125, PSA, erb-2 (Boon et al $Ann. Rev. Immunol.$ 12:337, 1994).

Tumor infiltrating lymphocytes (TILs) derived from tumor-bearing patients recognize tumor associated antigens presented by major histocompatibility complex (MHC) class I molecules. The infusion of TIL586 along with interleukin-2 (IL-2) into the autologous patient with metastatic melanoma resulted in the objective regression of tumor. A gene encoding a tumor antigen recognized by TIL586 was recently isolated and shown to encode gp75. The present invention is the identification and isolation of an antigenic peptide, MSLQRQFLR (SEQ ID NO.: 9), recognized by TIL586, which is not derived from the normal gp75 protein. Instead this nonamer peptide resulted from translation of an alternative open reading frame of the same gene. Thus, the gp75 gene encodes two completely different polypeptides, gp75 as an antigen recognized by IgG antibodies in sera from a patient with cancer, and a 24 amino acid product as a tumor rejection antigen recognized by T cells. This represents the first demonstration that a human tumor rejection antigen can be generated from a normal cellular gene using an open reading frame other than that used to encode the normal protein. These finding revealed a novel mechanism for generating tumor antigens, which may be useful as vaccines to induce tumor-specific cell-mediated immunity against cancer.

The method of ExoIII/S1 deletion analysis localized the cancer epitope in a small DNA fragment of the gp 75 gene. The cancer epitope was absent from the normal gp75 protein. The cancer peptide of the present invention recognized by TIL586 was derived from the gene product translated from an alternative open reading frame of the same gene encoding the normal gp 75 protein. Substitution of ATG with ATC at nucleotides 294–296 resulted in a complete loss of the ability to stimulate cytokine release from TIL586. Cold target inhibition experiments indicated that the identified cancer epitope was capable of competing for T cell recognition with a naturally processed peptide present on the tumor cells. Six T cell clones generated from the TIL586 cell line were capable of recognizing 586mel tumor cells, 586EBV B cells pulsed with this peptide and normal melanocytes in a HLA-A31 restricted fashion, also suggesting that the gene product encoded by the alternative open reading frame might be present in the tumor cells as well as the normal melanocytes.

The invention also provides a transgenic animal which has incorporated into its genome one or more copies of the alternative open reading frame DNA sequence encoding a cancer peptide or portion thereof. The general method of producing transgenic animals is described in Krimpenfort et al U.S. Pat. No. 5,175,384, Leder et al U.S. Pat. No. 5,175,383, Wagner et al U.S. Pat. No. 5,175,385, Evans et al U.S. Pat. No. 4,870,009 and Berns U.S. Pat. No. 5,174,986. The incorporation of the gene results in overexpression, altered expression or expression of multiple forms or variants of the cancer peptides. The resulting transgenic animal are useful in studies of the development of cancer. The animal model is useful in screening vaccines and chemotherapeutic drugs for cancer treatment.

This invention further comprises an antibody or antigen binding portion thereof elicited by immunization of the cancer peptide or antigenic cancer epitope of the present invention. In the case where the cancer peptide or antigenic cancer epitope is comprised of only a few amino acids, the cancer peptide or antigenic cancer epitope may be conjugated to a carrier protein in order to elicit an antibody response. Carrier proteins such as KLH, tetanus toxoid and the like and methods of conjugation are known in the art. The antibody has specificity for and reacts or binds with the cancer peptide and the antigenic cancer epitope of the present invention.

Exemplary antibody molecules are intact immunoglobulin molecules, substantially intact immunoglobulin molecules or these portions of an immunoglobulin molecule that contain the antigen binding site, including those portions of immunoglobulin molecules known in the art as F (ab), F (ab'), F (ab')$_2$, humanized chimeric antibody, and F (v). Polyclonal or monoclonal antibodies may be produced by methods known in the art. (Kohler and Milstein (1975) *Nature* 256, 495–497; Campbell "Monoclonal Antibody Technology, the Production and Characterization of Rodent and Human Hybridomas" in Burdon et al (eds.) (1985) "Laboratory Techniques in Biochemistry and Molecular Biolog", Vol. 13, Elsevier Science Publishers, Amsterdam). The antibodies or antigen binding fragments may also be produced by genetic engineering. The technology for expression of both heavy and light chain genes is the subject of the PCT patent applications: publication number WO 901443, WO 9014424, Huse et al (1989) *Science* 246: 1275–1281, and U.S. Pat. No. 4,946,778.

In one embodiment, the antibodies of the invention are used in immunoassays to detect cancer peptides or portions thereof in biological samples. The antibodies or antigen binding fragments thereof may be used to detect cancer peptides in tissue biopsy samples from a mammal afflicted with cancer. Assessment of the cancer antigen in a diseased tissue can be used to prognose the progression of the disease in a mammal or may diagnose the efficacy of a treatment. The immunoassay may be a radioimmunoassay. Western blot assay, immunofluorescent assay, enzyme immunoassay, chemiluminescent assay, immunohistochemical assay and the like and may be performed in vitro, in vivo or in situ. Standard techniques known in the art for ELISA are described in "Methods in Immunodiagnosis", 2nd Edition, Rose and Bigazzi, eds, John Wiley & Sons, 1980; Campbell et al "Methods and Immunology", W. A. Benjamin, Inc., 1964; and Oellerich, M. 1984, *J. Clin. Chem. Clin. Biochem.* 22:895–904. Conventional methods for immunohistochemistry are described in Harlow and Lane (eds) (1988) In "Antibodies A Laboratory Manual", Cold Spring Harbor Press, Cold Spring Harbor, N.Y.; Ausbel et al (eds) (1987) In Current Protocols In Molecular Biology, John Wiley and Sons (New York, N.Y.). Biological samples appropriate for such detection assays include but are not limited to cells, tissue biopsy, whole blood, plasma, serum, sputum, cerebrospinal fluid, pleural fluid, urine and the like.

The antibodies or antigen binding fragments of the present invention may also be used in immunotherapy. The antibodies or antigen binding fragment thereof is provided to a mammal in an amount sufficient to prevent, lessen or attenuate the severity, extent or duration of the cancer.

All articles and patents referred to are incorporated herein by reference.

While the invention is described above in relation to certain specific embodiments, it will be understood that many variations are possible, and that alternative materials and reagents can be used without departing from the invention. In some cases such variations and substitutions may require some experimentation, but will only involve routine testing.

The foregoing description of the specific embodiments will so fully reveal the general nature of the invention and others can, by applying current knowledge, readily modify and/or adopt for various applicants such specific embodiments without departing from the generic concept, and therefore such adaptations and modifications are intended to be comprehended within the meaning and range of equivalents of the disclosed embodiments.

EXAMPLE 1

Material and Methods

Chemicals and Reagents

The following chemicals and reagents were purchased from the sources indicated: RPMI 1640, AIM-V media, Lipofectamine, G418 (GIBCO BRL, Gaithersberg, Md.); the eukaryotic expression vector pCR3 (Invitrogen, San Diego, times with AIM-V medium containing 120 IU/ml of IL-2. TIL586 was added and incubated for additional 18–24 h, 100 µl of supernatant was collected for GM-CSF assay.

Exo III/S1 deletion constructions and PCR fragments

To make a series of deletions, the pcDNA776 plasmid DNA was digested with Xba I and filled in with alpha-phosphorothioate deoxyribonucleotide triphosphates to block Exo III nuclease digestion. The pcDNA776 plasmid is a derivative of the pcDNA3 vector containing a 2.4 kb DNA fragment and a CMV promoter for directing transcription. The linearized DNA was subjected to the second restriction enzyme Xho I digestion to generate one end sensitive to Exo III. Exo III nuclease/Mung bean nuclease deletion was performed according to the manufacture's instructions (Stratagene, Calif.) The detailed protocol is as follows:

1. 10 µg DNA was digested with XbaI and filled in with alpha-phosphorothioate deoxyribonucleotide.
2. The DNA was digested with the second enzyme XhoI followed by phenol extraction and ethanol precipitation.
3. DNA pellet was dried and suspended in 125 ul 2X Exo Buffer, 25 ul 100 mM β-mercaptoethanol, 100 ul water.
4. When al aliquots had been removed and placed on dry ice, the tubes were heated at 68° C. for 15 minutes, and then place on ice.
5. 15 U of Mung Bean Nuclease was added (previously diluted with 1X Mung Bean Dilution Buffer) to each time point tube and incubated for 30 minutes at 30° C.
6. The following were added:
    4 µl of 20% SDS
    10 µl 1M Tris-HCl, pH 9.5
    20 µl 8M LiCl
    250 µl buffer-equilibrated phenol:chloroform
7. Samples were vortexed, spun 1 minute in microfuge, upper aqueous layer was removed and extracted with chloroform to extract Mung Bean protein away from DNA.
8. 25 µl 3M NaOAc pH 7.0 was added to the aqueous phase. tRNA to a final concentration of 10 ng/µl was used as a carrier for the precipitation.

9. 650 μl of cold ethanol was added. Samples were chilled on dry ice 10 minutes and spun in a microfuge for 20 minutes.
10. The supernatant was drained off and the pellets washed with 80% ethanol.
11. The pellet was dried.
12. The DNA pellet was redissolve din 15 μl of 10 mM Tris-Cl pH 7.5, 0.1 mM EDTA.

B. Ligation

13. DNA deletions were ligated using the following conditions:
    1.0 μl Exo/Mung treated DNA
    2.0 μl 10X Ligation Buffer
        500 mM Tris-HCl, pH 7.5
        70 mM MgCl$_2$
        10 mM DTT
    2.0 μl 5 mM ATP, pH 7.0–7.5
    2.0 μl T4 DNA Ligase (Cat #600011; provided in kit)
    13.0 μH$_2$O
    20.0 μl Total Reaction Volume
    Incubated at room temperature
    Stratagene offers a DNA Ligation Kit (Cat #203003) for ligating inserts to vectors.
14. 7 μl of the remaining 14 μl of Exo/Mung treated DNA was used for gel electrophoresis analysis.
15. 1 μl of the ligation reaction was used to transform 100 μl of Epicurian coli RecA-JM109 or XL1-Blue cells and plate on LB/AMP plates.

C. Low Melting Agarose Technique

To minimize screening of deletions, a portion of the deletion was run in low melting point agarose, the band of interest excised and ligation continued. The agarose level was kept below 0.5% in the ligation reaction.

PCR amplification was performed at 94° C. for 2 min followed by 25 cycles of 94° C. for 1 min, 55° C. for 45 sec and 72° C. for 1 min. Primers gpN (5'AGAATGAGTGCTC-CTAAACTCCTCTCTCTGGG) (SEQ. ID NO: 42) and gp11B (5'CATGTGAGA AAAGCTGGTCCCTCA) (SEQ ID NO: 43) were used to generate the DNA fragment (1–667) and then cloned into the pCR3 expression vector to produce pPCR110. Plasmids pPCR210 and pPCR220 were pCR3 vectors containing DNA insertion fragments amplified by using primers gp-1 (5' TGGATATGGCAAAGCGC ACAACTC) (SEQ ID NO: 44) and gp11B, gp-1 and gp22 (5' TAAATGGAA ATGTTCTCAAATTGT GGCGTG) (SEQ. ID NO: 45), respectively.

Cytotoxic lysis assays

Cytolytic assays was done as previously described (Kawakami, Y et al., 1994, Proc. Natl. Acad. Sci. USA 91:6458–62). Briefly, the target cells were labeled with chromium for 90 min. After washing three times, the cells were incubated with peptides at a concentration of 1 μg/ml for 90 min. The cells were washed again, counted, and then mixed with TIL586 at the indicated ratio of effector : targets (E:T). Chromium release was measured after 4 h incubation. The peptides were synthesized by a solid-phase method using a peptide synthesizer (Model AMS 422, Gibson Co., Inc., Worthington, Ohio). Some peptides were purified by HPLC and had greater than 98% in purity. For titration of the ORF3P peptide recognized by TIL586, 586EBV B cells were incubated with various concentrations of the purified ORF3P peptide. Percentage of specific lysis was determined from the equation (A-B)/(C-B)×100 where A is lysis of 586EBV B cells by TIL586 in the presence of a peptide, B is spontaneous release from 586EBV B cells in presence of the same peptide but in the absence of effector cells, and C is the maximum chromium release. Cold target inhibition of cytolysis was performed using $^{51}$Cr-labeled 586mel or 624mel cells as "hot" targets and 586EBV B and T2 cells pulsed with peptides as "cold" targets.

Site-directed mutagenesis

For construction of sit-directed mutagenesis, mutated primers GPMUT1 were used. (5'GCCATGGGCAGAGAT-GATCGGGAGGTCTGGCCCTTGCGCTTCTTC AATAG-GACATCTCACTGCAAC) (SEQ. ID NO: 11) and GPA1 to generate a PCR fragment containing a mutation (G to C) at nucleotide 296. The wild-type DNA fragments were amplified by the use of primers GPF1 (5'GAAGATCTGC-CATGGGCAGAGATGTCGGGAGG TCTG) (SEQ ID NO: 12), GPE1 (5' GAATTCGTTG TGT CCTGAGAAATTGC-CGTTG) (SEQ. ID NO: 13), GPE2 (5'GA ATTCGACTAT-GAGAACCCTCTGGTCACAGGC) (SEQ. ID NO: 14) and GPA1 (5'AAGATCTGGGCC CGGACAAAGTGGT-TCTTTTC) (SEQ ID NO: 15) as indicated by arrowheads in FIG. 3A. The purified PCR products were then cloned into the pCR3 expression vector. All plasmids containing PCR fragments were sequenced to confirm the orientation and nucleotide sequence.

EXAMPLE 2

Localization of the Antigenic Peptide(s) Recognized by TIL586

Figure 1B:
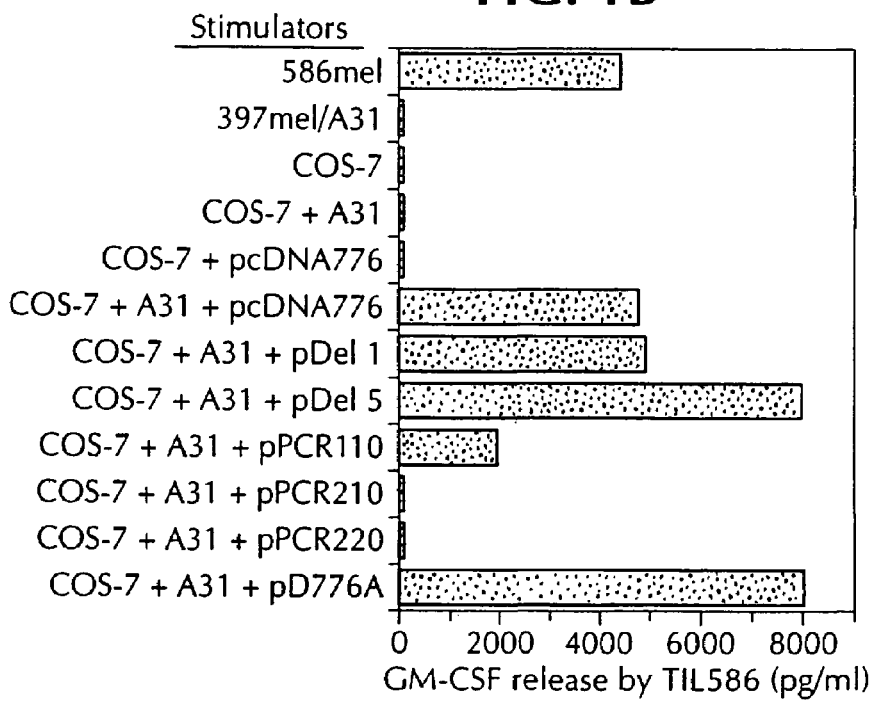

In order to identify the antigenic epitope from gp75, we generated a series of nested deletions of gp75 gene were generated from the 3' end using Exo III/S1 nuclease as well as additional DNA fragments from gp75 by PCR amplification (FIG. 1A). The reason pcDNA776 was chosen as a starting material for deletion studies is that this clone was initially identified by a library screening and conferred the ability to stimulate cytokine release from TIL586. Plasmid pcDNA776 was deposited with the American Type Culture Collection, 12301 Parklawn Drive, Rockville, Md. under the terms of the Budapest Treaty on Jan. 19, 1996 and was assigned the accession number, ATCC 97423. Since the goal of this study was to identify the epitope recognized by TIL586, fragments as short as possible were used (the truncated form of gp75, instead of full length cDNA) such that the epitope in a relative small DNA fragment could quickly be located. These deletions constructs were then transfected into COS-7 cells together with the pBK-CMV plasmid containing the HLA-A31 gene. (Wang, R. F. et al., 1995, J. Exp. Med. 181:799–804). After 24 hours, the transfected COS-7 cells were tested to determine which construct could stimulate cytokine release by TIL586. A small truncated DNA fragment ranging from nucleotide 247 to 771, which lacked the normal gp75 initiation codon, retained the ability to stimulate GM-CSF release by TIL586, suggesting that the epitope recognized by TIL586 was located in the DNA fragment containing nucleotides from 247 to 771. Since there is an ATG start codon in a relative good context of Kozak sequence (GATATGG) (SEQ. ID NO: 16) located at nucleotides 445–447 and is in the same frame as gp75 open reading frame, it was reasoned that the epitope recognized by TIL586 might be located in the region from nucleotide 445–771. Therefore, pPCR210 and pPCR220 were constructed, which were derivatives of the pCR3 expression vector and contained an internal ATG codon in frame with gp75 (GATATGG) (SEQ ID NO: 16) located at 445 bp as a start codon for translation of the truncated normal gp75 protein. However, neither pPCR210 nor pPCR220 conferred the ability to stimulate cytokine secretion from TIL586 after co-transfection of COS-7 with the HLA-A31 gene (FIG. 1B), suggesting that the epitope was located upstream of these fragments. Therefore, an additional plasmid pD776A was constructed, which contained the nucleotide sequence from 247–442 and did not have any ATG codon in the same frame as gp75, but did contain two ATG codons in different open reading frames relative to gp75. This plasmid strongly stimulated cytokine release from TIL586 when co-transfected with A31 cDNA into COS-7 cells. The plasmid pPCR110 containing the authentic start codon of gp75 stimulated several fold lower cytokine release than did pDel 5 or pD776A when co-transfected with the HLA-A31 gene (FIG. 1B). These results suggested that the epitope(s) recognized by TIL586 were located in the region from nucleotides 247 to 442.

Although this region (nucleotides 247–442) did not have any ATG start codon in the normal gp75 open reading frame, initiation of translation from the non-ATG codons such as ACG, CTG and GTG had been reported in some cases (Hann, S. R. 1994, *Biochimie* 76:880–86; Muralidhar, S. et al *J. Virol.* 1994, 68:170–76). To identify the epitope in this region, synthetic peptides were made based upon the peptide binding motif of HLA-A31 (hydrophobic residue at position 2 and positively charged residue at the C-terminus) (FIG. 2) (Falk, K. et al *Immunogenetics* 1994, 40:238–41). The majority of the peptides selected for this study were nonamers, although some were 10mers and 11mers. These peptides were pulsed onto 586EBV B cells and the ability of these cells to stimulate cytokine release by TIL586 (Table 1). One peptide, AACDQRVLIVRR (SEQ. ID NO: 25), very weakly induced GM-CSF release from TIL586. However, this peptide failed to sensitive peptide-loaded 586EBV B for lysis by TIL586 (Table 1).

TABLE 1

Screening of synthetic peptides with reactivity to TIL586

| | TIL586 | |
|---|---|---|
| Target cells pulsed with peptide | GM-CSF release | % Specific lysis (E:T 20:1) |
| Peptides from ORF1 (gp75) | | |
| 586EBV + peptide DDREVWPLR (Seq.ID No: 17) | <50 | <10 |
| 586EBV + peptide VWPLRFFNR (Seq.ID No: 18) | <50 | <10 |
| 586EBV + peptide SGHNCGTCR (Seq.ID No: 19) | <50 | <10 |
| 586EBV + peptide CGTCRPGWR (Seq.ID No: 20) | <50 | <10 |
| 586EBV + peptide ACDQRVLIVR (Seq.ID No: 21) | <50 | <10 |
| 586EBV + peptide ACDQRVLIVRR (Seq.ID No. 22) | <50 | <10 |
| 586EBV + peptide LWDVPSWLER (Seq.ID No. 23) | <50 | <10 |
| 586EBV + peptide AISQDTTVGR (Seq.ID No. 24) | <50 | <10 |
| 586EBV + peptide AACDQRVLIVR (Seq.ID No. 25) | 250 | <10 |
| 586EBV + peptide DQRVLIVRR (Seq.ID No. 26) | <50 | <10 |
| 586EBV + peptide IVRRNLLDLSK (Seq.ID No. 27) | <50 | <10 |
| 586EBV + peptide LSKEEKNHFVR (Seq.ID No. 28) | <50 | <10 |

TABLE 1-continued

Screening of synthetic peptides with reactivity to TIL586

| | TIL586 | |
|---|---|---|
| Target cells pulsed with peptide | GM-CSF release | % Specific lysis (E:T 20:1) |
| 586EBV + none | <50 | <10 |
| 586mel + none | >5000 | 45 |

586EBV cells were incubated with individual peptide at a concentration of 1 μg/ml for 90 min. GM-CSF release was measured after co-incubation of peptide-loaded 586EBV cells with TIL586. GM-CSF secretion by TIL586 alone without stimulators was subtracted. 586EBV was a EBV transformed B cell line expressing HLA-A-31. Cytotoxic lysis of peptide-pulsed 586EBV by TIL586 was done in a 4-h chromium release assay.

Because this peptide weakly stimulated cytokine release from TIL586 only when incubated 586EBV B cells at high concentrations (>1 μg/ml) and did not sensitize the target cells for lysis by TIL586 even at 10 μg/ml of peptide concentration (data not shown), it may not represented the predominant T cell epitope recognized by TIL586.

Figure 3A:
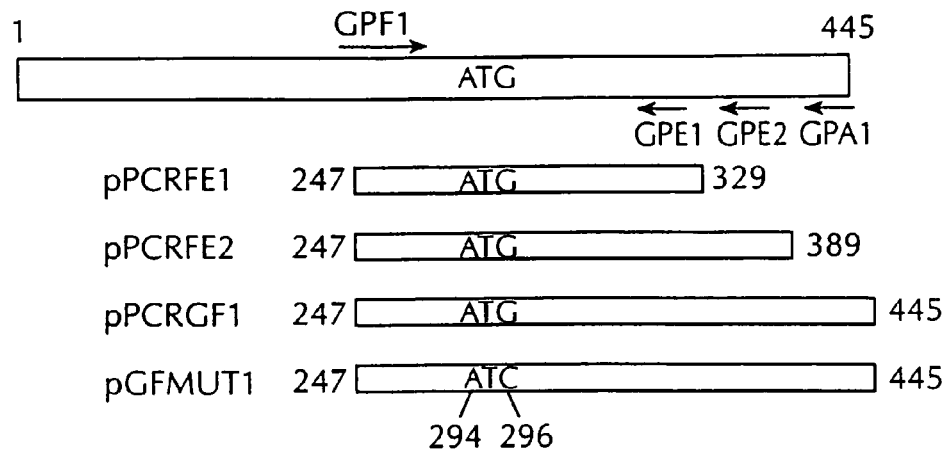
FIGS. 3A and 3B show an antigenic peptide and translation of an alternative open reading frame.
Figure 3B:
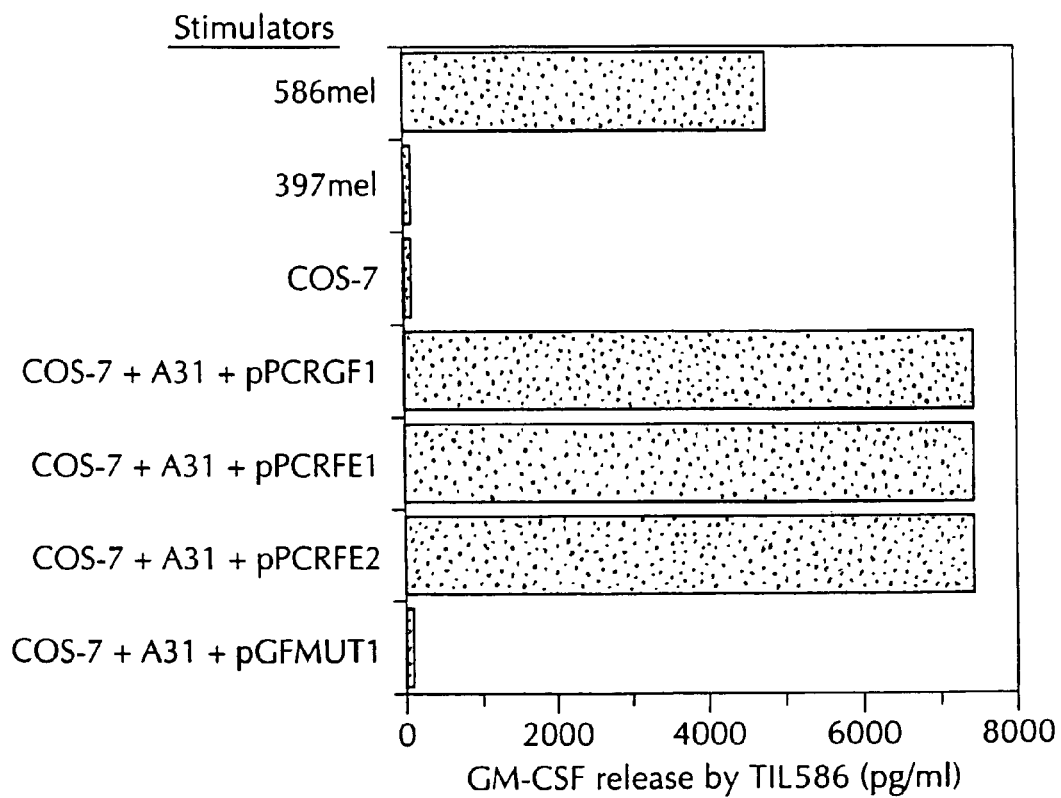

To further define the region containing the predominant T cell epitope, two additional plasmids were constructed containing PCR fragments amplified by primers GPF1, GPE1 and GPE2, respectively (FIG. 3A). As shown in FIG. 3B, both plasmids containing an ATG start codon at the beginning of the smaller PCR fragment conferred the ability to stimulate cytokine release by TIL586 in associated with HLA-A31 suggesting that the epitope recognized by T cells was encoded within an 82 nucleotide sequence between bases 247 and 329 of the gp75 cDNA. Twenty eight overlapping peptides (9 mers or 10 mers) in ORF1 were synthesized based upon the amino acid sequence of gp75 in this region, but none were found to stimulate GM-CSF release or sensitive 586EBV B cells for lysis by TIL586 (data not shown).

EXAMPLE 3

Figure 4A:
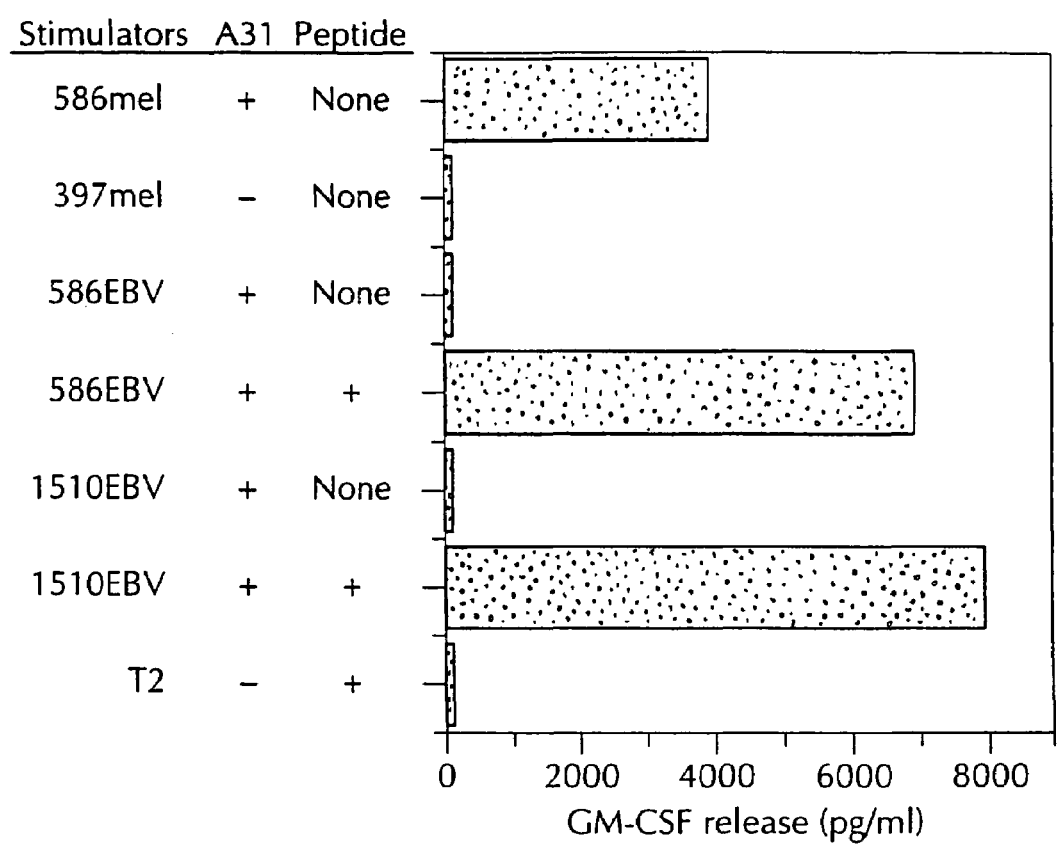
FIG. 4A–4C show characterization of the antigenic peptide recognized by TIL586.
Figure 4C:
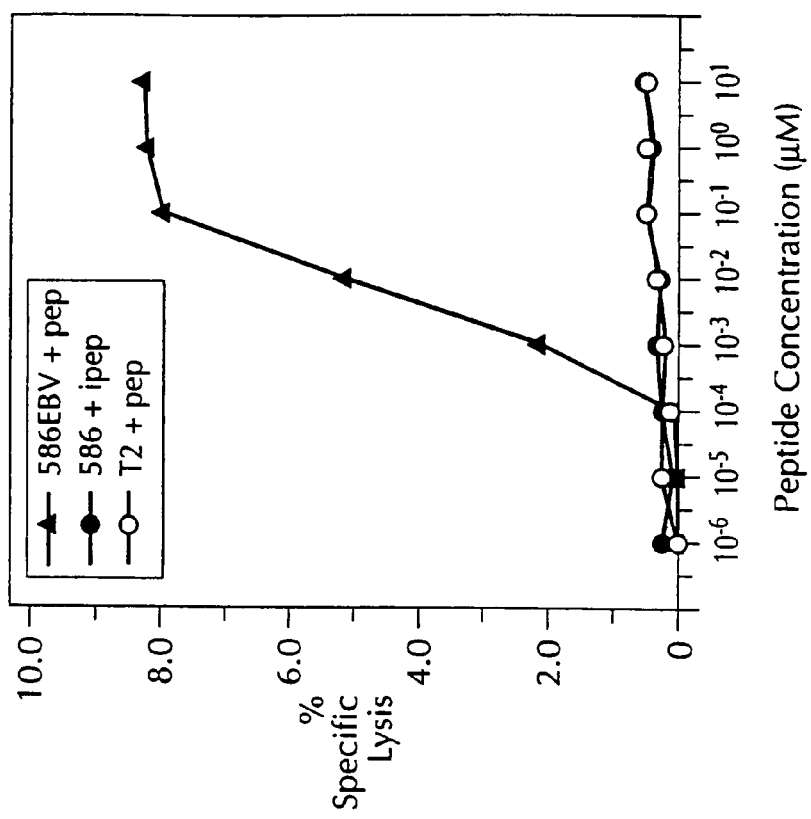
Figure 4B:
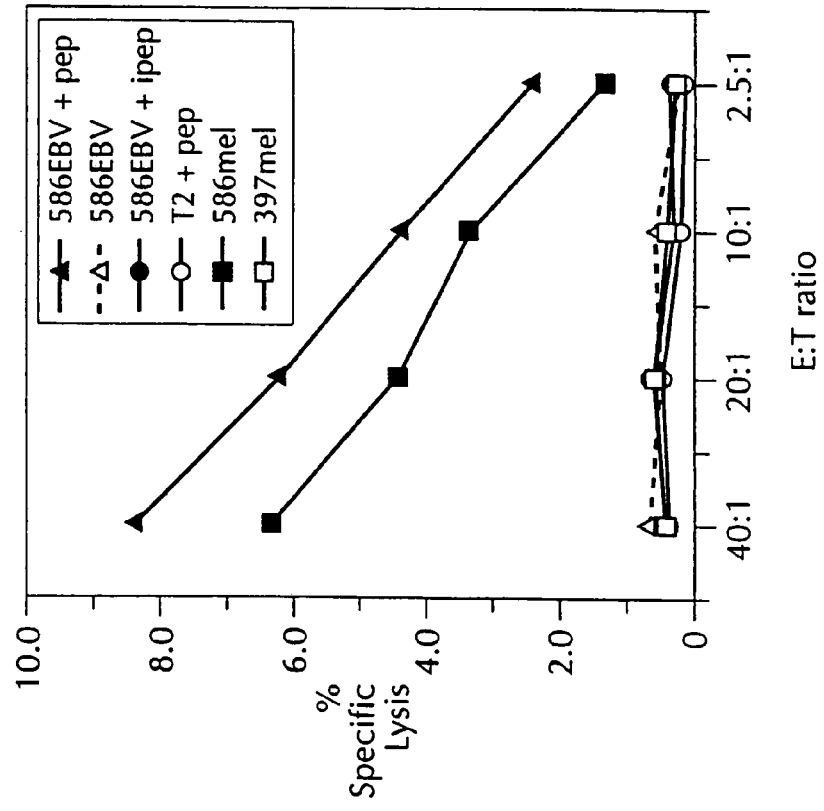

Antigenic Peptides resulted from Translation of an Alternative Open Reading Frame of the gp75 gene The failure to identify an epitope recognized by TIL586 in this small region suggested that alternative open reading frames might be translated. Two ATG codons in the relatively good context were present in this region (nucleotides 247–442) in different open reading frames relative to the gp75 open reading frame (ORF1) (FIG. 2). Translation from the first ATG (251 GAG<u>ATG</u>A257) (SEQ. ID NO:29) resulted in a open reading frame encoding 45 amino acids (ORF2) while translation starting from the ATG located between nucleotides 294–296 (GAC<u>ATG</u>T) (SEQ. ID NO: 30) generated a 24 amino acid gene product (ORF3) (FIG. 2). Three peptides derived from ORF2 and two peptides from ORF3 were selected and synthesized on the basis of the HLA-A31 binding motif (Table 2 and FIG. 2). Surprisingly, one peptide MSLQRQFLR (SEQ. ID NO: 9) (designated as ORF3P) which derived from ORF3 was strongly recognized by TIL586 when pulsed onto 586EBV B cells (Table 2). The recognition of the ORF3P peptide (MSLQRQFLR) (SEQ ID NO: 9) by TIL586 was observed only when the peptide was pulsed onto autologous 586EBV B cells and 1510EBV B (A31+) cells, but not when peptide was loaded onto T2 (non-HLA-A31) cells (FIG. 4A), suggesting that recognition of this peptide by TIL586 was HLA-A31 restricted. The peptide mass of ORF3P was confirmed by mass spectrometry analysis. As shown in FIG. 4B, TIL586 lysed 586EBV B cells pulsed with the ORF3P peptide, but failed to lyse 586EBV B cells pulsed with irrelevant peptide which met the criterion of the peptide binding motif of HLA-A31, but was not recognized by TIL586 or T2 cells pulsed with the ORF3P peptide. Sensitization for lysis by the peptide showed maximal effect at 100 nM, though lytic activity was detected even at 1 nM of peptide concentration (FIG. 4C). TIL586 did not recognize either peptides MSLQRQFLRT (SEQ ID NO: 33) or SLQRQFLRT (SEQ. ID NO: 34), or modified peptides (substitution of anchor residues at positions 2, 6 and 9) MLLQRQFLR (SEQ. ID NO: 36), M RLQRQFLR (SEQ. ID NO: 37), MSLQRLFLR (SEQ. ID NO: 38), MSLQRQFLE (SEQ. ID NO: 39), MSLQRQFLK (SEQ. ID NO: 40) derived from MSLQRQFLR (SEQ. ID NO: 9) (TABLE 2). TIL586 only recognized the peptide M ALQRQFLR (SEQ. ID NO: 35) with a substitution Ser with Ala at position 2 compared to the peptide MSLQRQFLR (SEQ. ID NO: 9) (Table 2). ORF3P peptide resulted from a frameshift. The DNA sequence analysis also confirmed that there was no deletion or insertion in the upstream region. To investigate if the ATG located at nucleotides 294–296 played an important role in translating the 24 amino acid product, ATGT (294–297) to ATCT were mutated (294–297) to eliminate the translation of ORF3, which would result in a change of Cys (UGU) to Ser (UVU) in ORF1 (gp75) (FIG. 3A). A plasmid containing the mutated gene (pGFMUT1) was tested for its ability to confer recognition by TIL586 when co-transfected into COS-7 along with the HLA-A31 cDNA. FIG. 3B showed that the mutated gene completely lost the ability to stimulate GM-CSF release by TIL586 compared to the construct containing the wild type gene. This observation indicated that ATG in ORF3 in the nucleotide positions 294–296 was required for translation of the 24 amino acid product, and therefore was essential for generating the T cell epitope recognized by TIL586.

Since the Met (ATG) is in position 1 of the peptide epitope and the mutation of ATG to ATC at nucleotides 294–296 resulted in a change of Met to Ile in position 1 of the peptide, the possibility that the loss of recognition of the mutated gene by TIL586 could be due to the loss of the ability of the mutated peptide to bind to MHC class I molecules were investigated. A synthetic peptide (ISLQRQFLR) (SEQ. ID NO: 41) with the same amino acid sequence as that encoded by the mutated gene was made and tested for recognition by TIL586. It was found that the synthetic mutated peptide was still recognized by TIL586 at comparable concentrations to that of the wild-type peptide. Furthermore, when the same mutation was introduced into the full length cDNA, no reactivity to TIL586 was observed whereas the wild-type cDNA was capable of stimulating cytokine release from TIL586 at a level similar to pPCR110. This is in agreement with the deletion data, indicating that ITL586 did not recognized peptide(s) in other regions of the gene. These results suggested that the loss of recognition of the mutated gene (ATG to ATC at nucleotides 294–296) by T cells was due to inactivation of translation initiation of ORF3.

EXAMPLE 4

Recognition of the Antigenic Peptide on Tumor Cells as well as Melanocytes

Figure 5A:
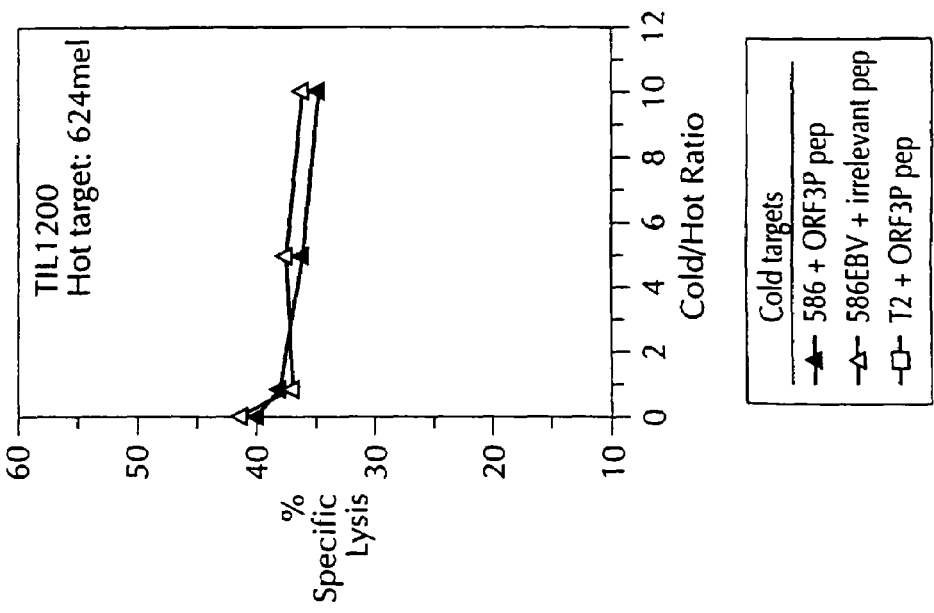
FIGS. 5A and 5B show inhibition of lysis of $^{51}$Cr-labeled target cells by non-labeled 586EBV cells loaded with the ORF3P peptide.
Figure 5B:
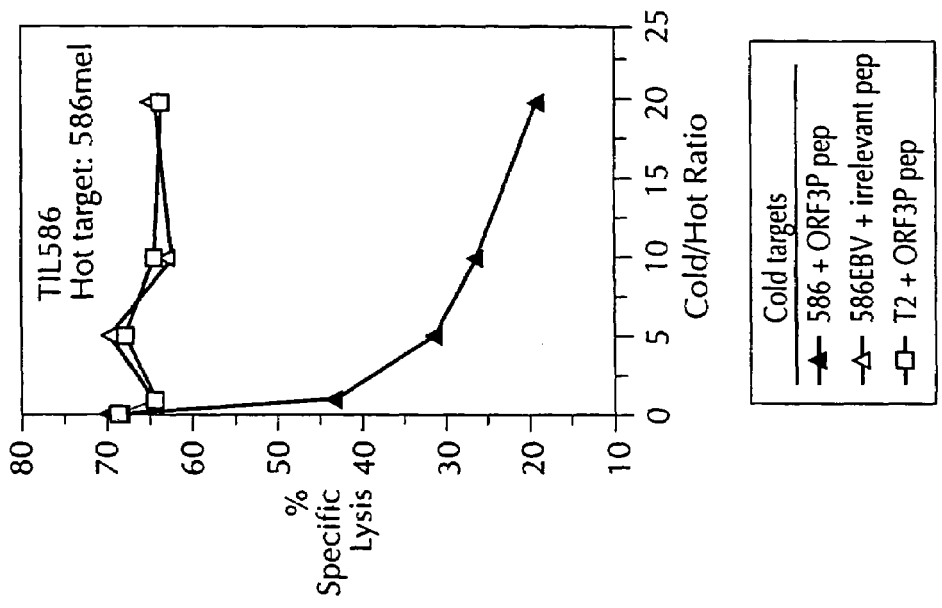
Figure 6A:
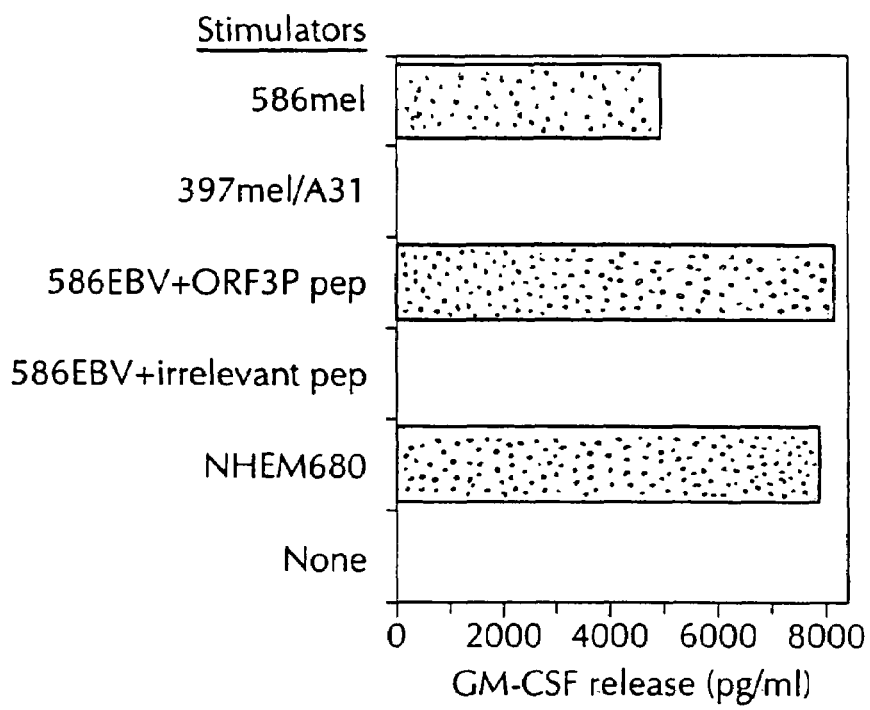
Figure 6B:
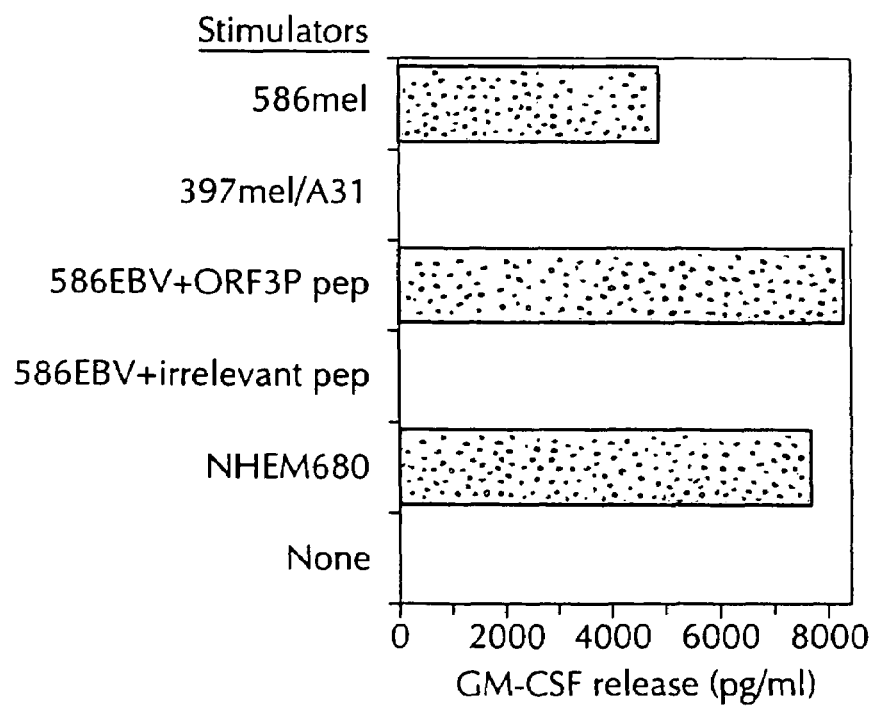
Figure 6C:
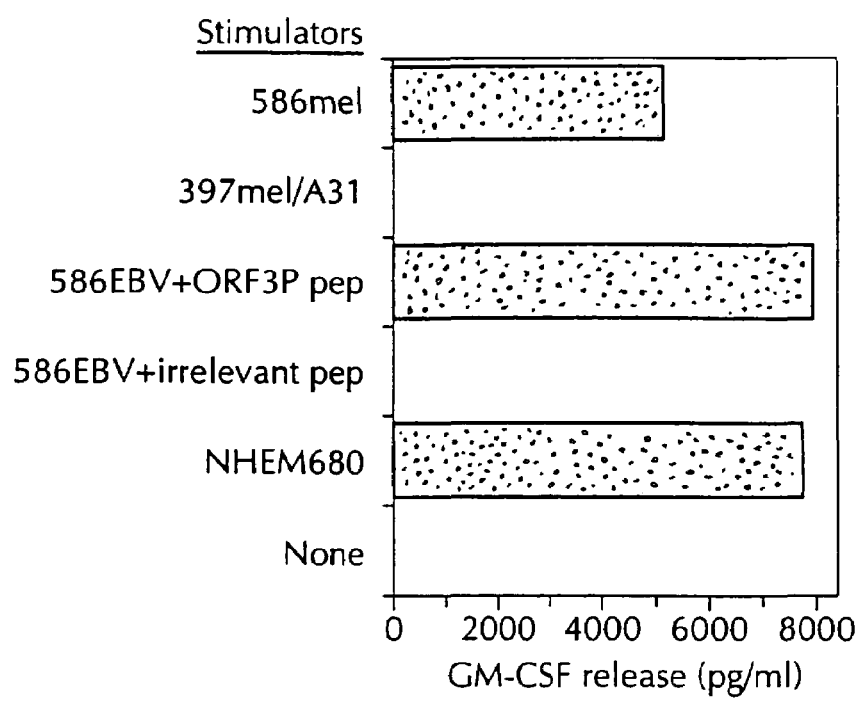
Figure 6D:
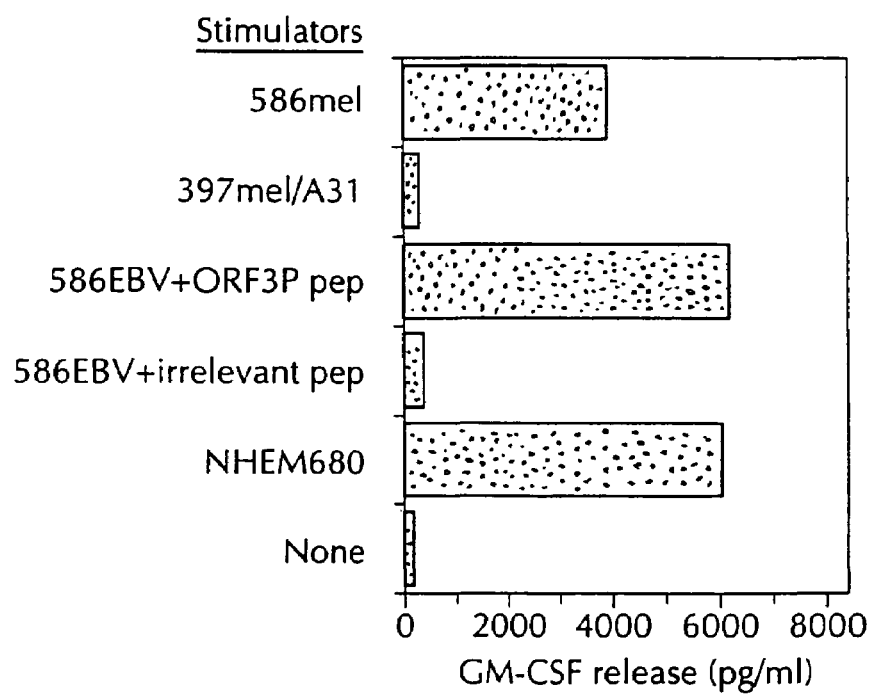

To address the question of whether TIL586 recognized a naturally processed peptide which is similar or identical to the ORF3P peptide on the tumor cells, the ability of the ORF3P peptide pulsed 586EBV B cells to inhibit lysis of $^{51}$Cr-labeled 586mel in a cold-target inhibition assay was examined. Significant inhibition of lysis of $^{51}$Cr-labeled 586mel was observed by 586EBV B cells pulsed with the ORF3P peptide but not with 586EBV B cells pulsed with irrelevant peptide or T2 cells pulsed with the ORF3P peptide (FIG. 5A), indicating that this peptide epitope was capable of competing with a naturally processed peptide on tumor cells for T cell recognition. As predicted, the ORF3P loaded 586EBV B cells did not inhibit lysis of target 624mel by TIL1200, which recognizes the gp100 antigen in the HLA-A2 context, compared to 586EBV B alone (FIG. 5B). To further test if T cell clones can recognize both the ORF3P peptide pulsed 586EBV B cells and tumor cell lines, T cell clones were generated from the TIL586 cell line by limiting dilution (1 cell/well in 96-well round bottom microplate) and further expanded in culture. T cell clones were generated by limiting dilution (1 cell per well) from the TIL586 cell line. T cell clones were further expanded in AIM-V medium containing 6000 IU/ml IL-2. 586EBV B cells were pulsed with the ORF3P peptide or irrelevant peptide for 90 min at 37° C. After washing three times, T cell clone or TIL586 cells were added and coincubated for additional 18–24 h. For 586 mel, 397 mel/A31$^+$ tumors and melanocyte NHEM680 cells, 1×10$^5$ cells per well were incubated with 1×10$^5$ cells to T cell clones, TIL586-C1 (FIG. 6A), TIL586-C4 (FIG. 6B) and TIL586-C6 (FIG. 6C) or TIL586 (FIG. 6D) for 18–24 h, respectively. GM-CSF assay was performed as described in FIG. 1B Six T cell clones were capable of recognizing 586 mel tumor cells, 586EBV B cells pulsed with the ORF3P peptide, and HLA-A31 positive melanocytes, but not 397 mel/A31 or 586EBV B cells alone. Representative data is shown in FIGS. 6A–6D. These results suggested that T cell clones probably recognized a naturally processed peptide either similar or identical to the ORF3P peptide on tumor cells and normal melanocytes.

Since there is a 40–45% amino acid sequence identity of gp75 to tyrosinase, gp100 and TRP-2, the possibility that the peptide recognized by the T cell clones was not derived from gp75, but from one of these other proteins was tested. COS-7 cells were transfected with HLA-A31 plus tyrosinase, gp100 or TRP-2 cDNAs, respectively, and found that none could be recognized by the six T clones while the COS-7 transfected HLA-A31 and gp75 cDNA stimulated GM-CSF release from these clones (data not shown). A computer database search also indicated that no known proteins including tyrosinase, gp100 and TRP-2 in the database contained amino acid sequences with the peptide binding motif of HLA-A31 and significant similarity to the peptide epitope recognized by TIL586.

EXAMPLE 5

In vivo Protection Assay

For in vivo protection studies, MHL-A31$^+$ transgenic mice are immunized with 0, 1 pg, 1 ng, 1 µg, 1 mg or 100 mg of cancer peptide (SEQ ID NO: 9), intravenously at day zero and day 14 before a subcutaneous challenge with 10$^4$ Trp-1$^+$B16 mouse melanoma cells or intravenous challenge with 5×10$^5$ Trp-2$^+$ B16 mouse melanoma cells. Mice receiving tumor cells subcutaneously are observed twice a week for tumor development and the size determined. Mice receiving tumor cells intravenously are euthanized on day 12 and the number of lung metastases determined as described by Houghton, A. N. 1994 *J. Exp. Med.* 180:1–40.

EXAMPLE 6

In vivo Treatment Assay

For in vivo treatment, MHL-A31$^+$ transgenic mice are challenged with either 1×10$^5$ or 5×10$^5$ Trp-1$^+$ B16 mouse melanoma cells intravenously in order to establish pulmonary metastases. Mice are subsequently vaccinated with a recombinant virus expressing cancer peptide (SEQ. ID NO: 9) at 10$^5$ PFU/mg body weight. Mice are euthanized on day 12 and the number of pulmonary metastases in vaccinated mice vs. non-vaccinated mice determined.

EXAMPLE 7

Cancer Antigen Specific T Lymphocytes Immunotherapy

T-lymphocytes presensitized to a melanoma antigen may be effective in therapeutically treating mammals afflicted with a melanoma. T-lymphocytes are isolated from peripheral blood or melanoma tumor suspensions and cultured in vitro (Kawakami, Y. et al., 1988, *J. Exp. Med.* 168:2183–2191).

The T lymphocytes are exposed to the cancer peptide (SEQ. ID NO: 6) at a concentration of 1 µg/ml alone or in the presence of IL-2, resensitized and expanded in culture. T-lymphocytes exposed to the cancer peptide are administered to a mammal at about 10$^9$ to 10$^{12}$ lymphocytes per mammal. The lymphocytes are administered either intravenously, intraperitoneally or intralesionally. The treatment may be administered concurrently with other therapeutic treatments such as cytokines, surgical excision of melanoma lesions and chemotherapeutic drugs.

EXAMPLE

Treatment of Patients with Metastatic Melanoma

In this protocol, patients with advanced melanoma are immunized with an antigenic cancer epitope.

Patients eligible for the trial must have evidence of measurable or evaluable metastatic melanoma that has failed standard effective therapy. Patients must have tumors that express the TPI-1 antigen as evidenced by PCR or Northern Blot analysis of tumor cell RNA.

Patients receive either 1 ng, 1 µg, 1 mg or 500 mg/kg body weight of a cancer peptide (SEQ. ID NO: 6) via intravenously at day zero, day 7 and day 14 alone or in combination with IL2 and/or an immunostimulatory molecule. Patients are evaluated for toxicity, immunologic effects and therapeutic efficacy.

Lymphocytes taken from the treated patients are tested for specific response to the cancer antigen comprising the amino acid sequence MSLQRQFLR (SEQ. ID NO: 6).

A complete response is defined as the disappearance of all clinical evidence of disease that lasts at least four weeks. A partial response is a 50% or greater decrease in the sum of the products of the perpendicular diameter of all measurable lesions for at least four weeks with no appearance of new lesions or increase in any lesions. Minor responses are defined as 25–49% decrease in the sum of the products of the perpendicular diameters of all measurable lesions with no appearance of new lesions and no increase in any lesions. Any patient with less than a partial response is considered a non-responder. The appearance of new lesions or greater than 25% increase in the product of perpendicular diameters of prior lesions following a partial or complete response is considered as a relapse.

Discussion

Several antigenic T-cell epitopes derived from the normal open reading frame of the corresponding non-mutated shared melanoma antigens such as tyrosinase, MART-1/Melan-A and gp100 have been identified. In this study, it was demonstrated that the antigenic peptide recognized by TIL586 was derived from a second gene product of the gp75 gene. To our knowledge, this is the first example that T cells recognize an antigenic peptide resulting from the translation of an overlapping open reading frame of the same gene and the only example in eukaryotic cells that two completely different proteins and/or peptides can be translated from overlapping open reading frames of a single cellular gene. The ORF3 of the gp75 gene encodes a short protein of 24 amino acid. The antigenic peptide recognized by TIL586 is encoded by the sequence located immediately behind the ATG (294–296) start codon of the alternative open reading frame.

Although gp75 shares a 40–45% sequence homology to tyrosinase, gp100 and TRP-2, co-transfection of HLA-A31 and tyrosinase, gp100 or TRP-2 cDNAs, respectively, into COS-7 cells failed to stimulate GM-CSF release from T cell clones derived from TIL586. A database search did not reveal any proteins that had the HLA-A31 peptide binding motif and significant sequence homology to the peptide epitope recognized by TIL586 and its derived T cell clones. In addition, previous studies showed that melanoma transfectants (gp75$^+$/A31$^+$) conferred the ability to stimulate GM-CSF release from TIL586, but gp75 melanoma transfectants (gp75/A31$^+$) did not (Wang, R. F. et al 1995 *J. Exp. Med.* 181:799–804). Similar results were obtained with additional melanoma cell lines (gp75/A31$^+$). These results suggested that it was unlikely that TIL586 recognized the epitope peptide derived from other known genes. Since the ORF3P peptide was only epitope identified from the gp75 gene and was recognized by six T cell clones derived from TIL586, this peptide may be identical or similar to the naturally processed peptide on tumor cells and melanocytes. This was further supported by cold-target inhibition experiments since this peptide was capable of competing for T cell recognition with a natural peptide on tumor cells.

It was reported that T-cell epitope peptides derived from the frameshift of the mutated adenomatosis polyposis coli (APC) gene in colon cancer were recognized by CTLs generated from vaccinated BALB/c mice (Townsend, A. et al 1994 *Nature* 371:662). The results in FIG. 3 indicated that the ATG at nucleotides 294–296 was required for translation of the 24 amino acid product which, in turn, was processed to the antigenic peptide recognized by TIL586. TIL586 still recognized the mutated synthetic peptide pulsed on 586EBV B cells, but not the mutated gene when co-transfected into COS-7 cells with HLA-A31 cDNA, indicating that the loss of recognition of the mutated (ATG to ATC) gene by TIL586 resulted from elimination of translation of the ORF3 product. These results plus DNA sequence analysis ruled out the possibility that the antigenic peptide recognized by TIL586 was derived from the frameshift product of gp75. It is possible, therefore, that multiple peptides or proteins are often translated from overlapping open reading frames of a single eukaryotic gene, but that means to detect these alternate products have not been available. The exquisite sensitivity of T cells to detect naturally processed peptides may reveal many other examples of this phenomenon.

The mechanism by which the overlapping open reading frame 3 (ORF3) is translated in vivo is currently unclear. Although examples have been reported of cellular mRNAs that initiate at more than one AUG codon, and that, in some rare cases, initiate at both AUG and non-AUG codons such as CUG to generate N-terminally extended identical sequences, the use of overlapping open reading frames (i.e. translating two completely dissimilar peptides) from a single eukaryotic cellular mRNA has never been described to our knowledge. Several examples of translation of overlapping reading frames from a single mRNA have been described, but exclusively limited to viral genes. The detection of the products of overlapping reading frames in viral genes have been possible because of the existence of reactive antibodies in the sera of virally infected hosts. In the present invention a T cell assay was used to identify the epitope peptide recognized by T cells. This approach is very different from and more sensitive than conventional Western blots or immunoprecipitation analyses. Although there are five ATG codons between the authentic start codon and the start codon of ORF3, the construct pPCR110 covering the N-terminal part of ORF1 (gp75), the entire ORF2 and ORF3 (nucleotides 1-667) still retained the ability to stimulate cytokine release from TIL586. The level of stimulation, however, was several fold lower than that stimulated by the 5' truncated (lacking the first 246 nucleotides) form of gp75 (FIG. 1A and 1B), suggesting that the upstream ATG codons may have partially inhibited the expression of ORF3. Several factors have made it possible to detect the expression of the ORF3 product in this system. First, the upstream ATG codons proceeding the ATG start codon of ORF3 did not appear to be in the optimal context, which may allow to use the downstream ATG as start codons by the leaky scanning model. Second, the relative high expression of transfected genes in COS-7 cells and the availability of the T cell assay as an extremely sensitive means may allow detection of very low levels of the translated products.

Interestingly, the ORF3 product was detected by T cells in the tumor cells as well as normal melanocytes (FIGS. 6A–6D), strongly suggesting that the ORF3 protein was not a gene product resulted from genetic alterations in tumor cells. In the previous studies, it was shown that TIL586 recognized multiple tumor cell lines (gp75$^+$/A31$^+$) tested, suggesting that TIL586 recognizes a non-mutated, shared tumor antigen (Wang R. F. et al., ibid). Since the gp75 gene is highly expressed in melanomas based on Northern blot and PCR analyses (Wang R. F. et al, ibid) and its gene product gp75 protein is the most abundant intracellular glycoprotein expressed in melanoma cells and melanocytes (Tai, T., Eisinger, M., Ogata, S. and Lloyd, K. O, 1983, *Cancer Res.* 43: 2773–2779; Thomson, T. N., Mattes, J. M., Roux, L., Old L. J. and Lloyd, K. O. 1985, *J. Invest. Dermat.* 85, 169–174; Thomson, T. N., real. F. X., Mutakami, S., Cordon-carbo, C., Old, L. J. and Houghton, A. N. 1988, *J. Invest. Dermat.* 90, 459–466), it is not surprising that the T cell clones recognized the ORF3P peptide when pulsed onto 586EBV B cells (A31$^+$), melanoma (gp75$^+$/A31$^+$) as well as A31$^+$ melanoma cells or ORF3P pulsed on non-A31 T2 cells. Another possibility to explain the peptide expression in tumor cells and melanocytes is that the ORF3 may be translated from a separate mRNA transcript(s) generated by an alternative splicing of gp75 mRNA or a different promoter. To our knowledge, mRNA transcripts generated by alternative splicing are translated into isoform proteins by use of the same open reading frames. In our case, however, if a separate transcript was generated and used as a template for translation, but a completely different open reading frame relative to gp75 was used to translated ORF3 product. Further experiments are needed to clarify the mechanisms for the translation of the ORF3 protein in vivo. Nevertheless, these possibilities mentioned above are not mutually exclusive.

We claim:

1. An isolated antibody, or antigen binding portion thereof, which antibody or portion thereof, binds to an epitope in SEQ ID NO: 6.

2. The isolated antibody or antigen binding portion thereof according to claim 1, which binds an epitope encoded by SEQ ID NO: 10.

3. The isolated antibody or antigen binding portion thereof according to claim 1, which binds an epitope in SEQ ID NO: 9.

4. An isolated antibody or antigen binding portion thereof elicited by immunization with a cancer peptide consisting of the amino acid sequence of SEQ ID NO: 6 or SEQ ID NO: 7, or an immunizing portion of either of the foregoing, wherein the isolated antibody or antigen binding portion thereof binds to SEQ ID NO: 6 or SEQ ID NO: 7.

5. A composition comprising the isolated antibody or antigen binding portion thereof according to any one of claims 1, 2, and 3 and a pharmaceutically acceptable carrier.

6. A kit comprising the isolated antibody or antigen binding portion thereof according to any one of claims 1, 2, and 3.

7. A kit according to claim 6 further comprising standard immunoassay reagents.

8. An isolated antibody, or antigen binding portion thereof, which antibody or portion thereof, binds to an epitope in SEQ ID NO: 7.

9. The isolated antibody or antigen binding portion thereof according to claim 8, wherein the epitope is SEQ ID NO; 8.

10. A composition comprising the isolated antibody or antigen binding portion thereof according to claim 8 and a pharmaceutically acceptable carrier.

11. A kit comprising the isolated antibody or antigen binding portion thereof according to claim 8.

12. The kit according to claim 11 further comprising standard immunoassay reagents.

13. A composition comprising the isolated antibody or antigen binding portion thereof according to claim 4 and a pharmaceutically acceptable carrier.

14. A kit comprising the isolated antibody or antigen binding portion thereof according to claim 4.

15. A kit according to claim 14 further comprising standard immunoassay reagents.

* * * * *

UNITED STATES PATENT AND TRADEMARK OFFICE
CERTIFICATE OF CORRECTION

PATENT NO.        : 7,015,312 B1
APPLICATION NO.   : 09/571313
DATED             : March 21, 2006
INVENTOR(S)       : Wang et al.

It is certified that error appears in the above-identified patent and that said Letters Patent is hereby corrected as shown below:

IN THE TITLE PAGE:

Item (73) Assignee: "The United States of America as represented by the Department of Health and Human Services, Washington, DC (US)" should read --Government of the United States of America, represented by the Secretary, Department of Health and Human Services, Rockville, MD (US)--.

Signed and Sealed this

First Day of August, 2006

JON W. DUDAS
*Director of the United States Patent and Trademark Office*

SEQUENCE LISTING

```
<160> NUMBER OF SEQ ID NOS: 46

<210> SEQ ID NO 1
<211> LENGTH: 471
<212> TYPE: DNA
<213> ORGANISM: Homo sapiens
<220> FEATURE:
<221> NAME/KEY: CDS
<222> LOCATION: (1)..(471)
<223> OTHER INFORMATION:
<300> PUBLICATION INFORMATION:
<301> AUTHORS: Cohen, T., et al.
<302> TITLE: NUCLEOTIDE SEQUENCE OF THE cDNA ENCODING HUMAN
      TYROSINASE-RELATED PROTEIN
<303> JOURNAL: NUCLEIC ACIDS RESEARCH
<304> VOLUME: 18
<305> ISSUE: 9
<306> PAGES: 2807-2808
<307> DATE: 1990-05-11
<308> DATABASE ACCESSION NUMBER: EMBL/X51420
<309> DATABASE ENTRY DATE: 1995-03-23
<313> RELEVANT RESIDUES: (1)..(471)

<400> SEQUENCE: 1 atg agt gct cct aaa ctc ctc tct ctg ggc tgt atc ttc ttc ccc ttg      48
Met Ser Ala Pro Lys Leu Leu Ser Leu Gly Cys Ile Phe Phe Pro Leu
1               5                   10                  15
```

```
cta ctt ttt cag cag gcc cgg gct caa ttc cca aga cag tgt gcc act        96
Leu Leu Phe Gln Gln Ala Arg Ala Gln Phe Pro Arg Gln Cys Ala Thr
        20                  25                  30 gtt gag gct ttg aga agt ggt atg tgt tgc cca gac ctg tcc cct gtg       144
Val Glu Ala Leu Arg Ser Gly Met Cys Cys Pro Asp Leu Ser Pro Val
        35                  40                  45 tct ggg cct ggg aca gac cgc tgt ggc tca tca ggg agg ggc aga           192
Ser Gly Pro Gly Thr Asp Arg Cys Gly Ser Ser Gly Arg Gly Arg
50                      55                  60 tgt gag gca gtg act gca gac tcc cgg ccc cac agc cct cag tat ccc       240
Cys Glu Ala Val Thr Ala Asp Ser Arg Pro His Ser Pro Gln Tyr Pro
65                  70                  75                  80 cat gat ggc aga gat gat cgg gag gtc tgg ccc ttg cgc ttc ttc aat       288
His Asp Gly Arg Asp Asp Arg Glu Val Trp Pro Leu Arg Phe Phe Asn
                85                  90                  95 agg aca tgt cac tgc aac ggc aat ttc tca gga cac aac tgt ggg acg       336
Arg Thr Cys His Cys Asn Gly Asn Phe Ser Gly His Asn Cys Gly Thr
            100                 105                 110 tgc cgt cct ggc tgg aga gga gct gcc tgt gac cag agg gtt ctc ata       384
Cys Arg Pro Gly Trp Arg Gly Ala Ala Cys Asp Gln Arg Val Leu Ile
        115                 120                 125 gtc agg aga aat ctt ctg gac tta agt aaa gaa gaa aag aac cac ttt       432
Val Arg Arg Asn Leu Leu Asp Leu Ser Lys Glu Glu Lys Asn His Phe
130                 135                 140 gtc cgg gcc ctg gat atg gca aag cgc aca act cac cct                   471
Val Arg Ala Leu Asp Met Ala Lys Arg Thr Thr His Pro
145                 150                 155

<210> SEQ ID NO 2
<211> LENGTH: 157
<212> TYPE: PRT
<213> ORGANISM: Homo sapiens

<400> SEQUENCE: 2

Met Ser Ala Pro Lys Leu Leu Ser Leu Gly Cys Ile Phe Phe Pro Leu
1               5                   10                  15

Leu Leu Phe Gln Gln Ala Arg Ala Gln Phe Pro Arg Gln Cys Ala Thr
            20                  25                  30

Val Glu Ala Leu Arg Ser Gly Met Cys Cys Pro Asp Leu Ser Pro Val
        35                  40                  45

Ser Gly Pro Gly Thr Asp Arg Cys Gly Ser Ser Gly Arg Gly Arg
    50                  55                  60

Cys Glu Ala Val Thr Ala Asp Ser Arg Pro His Ser Pro Gln Tyr Pro
65                  70                  75                  80

His Asp Gly Arg Asp Asp Arg Glu Val Trp Pro Leu Arg Phe Phe Asn
                85                  90                  95

Arg Thr Cys His Cys Asn Gly Asn Phe Ser Gly His Asn Cys Gly Thr
            100                 105                 110

Cys Arg Pro Gly Trp Arg Gly Ala Ala Cys Asp Gln Arg Val Leu Ile
        115                 120                 125

Val Arg Arg Asn Leu Leu Asp Leu Ser Lys Glu Glu Lys Asn His Phe
130                 135                 140

Val Arg Ala Leu Asp Met Ala Lys Arg Thr Thr His Pro
145                 150                 155

<210> SEQ ID NO 3
<211> LENGTH: 129
<212> TYPE: DNA
<213> ORGANISM: Homo sapiens
```

-continued

```
<220> FEATURE:
<221> NAME/KEY: CDS
<222> LOCATION: (1)..(129)
<223> OTHER INFORMATION:

<400> SEQUENCE: 3 atg atc ggg agg tct ggc cct tgc gct tct tca ata gga cat gtc act      48
Met Ile Gly Arg Ser Gly Pro Cys Ala Ser Ser Ile Gly His Val Thr
1               5                   10                  15 gca acg gca att tct cag gac aca act gtg gga cgt gcc gtc ctg gct      96
Ala Thr Ala Ile Ser Gln Asp Thr Thr Val Gly Arg Ala Val Leu Ala
                20                  25                  30 gga gag gag ctg cct gtg acc aga ggg ttc tca                         129
Gly Glu Glu Leu Pro Val Thr Arg Gly Phe Ser
            35                  40

<210> SEQ ID NO 4
<211> LENGTH: 43
<212> TYPE: PRT
<213> ORGANISM: Homo sapiens

<400> SEQUENCE: 4

Met Ile Gly Arg Ser Gly Pro Cys Ala Ser Ser Ile Gly His Val Thr
1               5                   10                  15

Ala Thr Ala Ile Ser Gln Asp Thr Thr Val Gly Arg Ala Val Leu Ala
                20                  25                  30

Gly Glu Glu Leu Pro Val Thr Arg Gly Phe Ser
            35                  40

<210> SEQ ID NO 5
<211> LENGTH: 72
<212> TYPE: DNA
<213> ORGANISM: Homo sapiens
<220> FEATURE:
<221> NAME/KEY: CDS
<222> LOCATION: (1)..(72)
<223> OTHER INFORMATION:

<400> SEQUENCE: 5 atg tca ctg caa cgg caa ttt ctc agg aca caa ctg tgg gac gtg ccg      48
Met Ser Leu Gln Arg Gln Phe Leu Arg Thr Gln Leu Trp Asp Val Pro
1               5                   10                  15 tcc tgg ctg gag agg agc tgc ctg                                      72
Ser Trp Leu Glu Arg Ser Cys Leu
            20

<210> SEQ ID NO 6
<211> LENGTH: 24
<212> TYPE: PRT
<213> ORGANISM: Homo sapiens

<400> SEQUENCE: 6

Met Ser Leu Gln Arg Gln Phe Leu Arg Thr Gln Leu Trp Asp Val Pro
1               5                   10                  15

Ser Trp Leu Glu Arg Ser Cys Leu
            20

<210> SEQ ID NO 7
<211> LENGTH: 24
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa= Ser or Ala
```

```
<400> SEQUENCE: 7

Met Xaa Leu Gln Arg Gln Phe Leu Arg Thr Gln Leu Trp Asp Val Pro
1               5                   10                  15

Ser Trp Leu Glu Arg Ser Cys Leu
            20

<210> SEQ ID NO 8
<211> LENGTH: 9
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa = Ser or Ala

<400> SEQUENCE: 8

Met Xaa Leu Gln Arg Gln Phe Leu Arg
1               5

<210> SEQ ID NO 9
<211> LENGTH: 9
<212> TYPE: PRT
<213> ORGANISM: Homo sapiens

<400> SEQUENCE: 9

Met Ser Leu Gln Arg Gln Phe Leu Arg
1               5

<210> SEQ ID NO 10
<211> LENGTH: 27
<212> TYPE: DNA
<213> ORGANISM: Homo sapiens

<400> SEQUENCE: 10
atgtcactgc aacggcaatt tctcagg                                      27

<210> SEQ ID NO 11
<211> LENGTH: 66
<212> TYPE: DNA
<213> ORGANISM: Homo sapiens

<400> SEQUENCE: 11
gccatgggca gagatgatcg ggaggtctgg cccttgcgct tcttcaatag gacatctcac   60
tgcaac                                                             66

<210> SEQ ID NO 12
<211> LENGTH: 37
<212> TYPE: DNA
<213> ORGANISM: Homo sapiens

<400> SEQUENCE: 12
gaagatctgc catgggcaga gatgatcggg aggtctg                           37

<210> SEQ ID NO 13
<211> LENGTH: 31
<212> TYPE: DNA
<213> ORGANISM: Homo sapiens

<400> SEQUENCE: 13
gaattcgttg tgtcctgaga aattgccgtt g                                 31

<210> SEQ ID NO 14
```

```
<211> LENGTH: 33
<212> TYPE: DNA
<213> ORGANISM: Homo sapiens

<400> SEQUENCE: 14
gaattcgact atgagaaccc tctggtcaca ggc                              33

<210> SEQ ID NO 15
<211> LENGTH: 32
<212> TYPE: DNA
<213> ORGANISM: Homo sapiens

<400> SEQUENCE: 15
aagatctggg cccggacaaa gtggttcttt tc                               32

<210> SEQ ID NO 16
<211> LENGTH: 7
<212> TYPE: DNA
<213> ORGANISM: Homo sapiens

<400> SEQUENCE: 16 gatatgg                                                            7

<210> SEQ ID NO 17
<211> LENGTH: 9
<212> TYPE: PRT
<213> ORGANISM: Homo sapiens

<400> SEQUENCE: 17

Asp Asp Arg Glu Val Trp Pro Leu Arg
1               5

<210> SEQ ID NO 18
<211> LENGTH: 9
<212> TYPE: PRT
<213> ORGANISM: Homo sapiens

<400> SEQUENCE: 18

Val Trp Pro Leu Arg Phe Phe Asn Arg
1               5

<210> SEQ ID NO 19
<211> LENGTH: 9
<212> TYPE: PRT
<213> ORGANISM: Homo sapiens

<400> SEQUENCE: 19

Ser Gly His Asn Cys Gly Thr Cys Arg
1               5

<210> SEQ ID NO 20
<211> LENGTH: 9
<212> TYPE: PRT
<213> ORGANISM: Homo sapiens

<400> SEQUENCE: 20

Cys Gly Thr Cys Arg Pro Gly Trp Arg
1               5

<210> SEQ ID NO 21
<211> LENGTH: 10
<212> TYPE: PRT
<213> ORGANISM: Homo sapiens

<400> SEQUENCE: 21
```

```
Ala Cys Asp Gln Arg Val Leu Ile Val Arg
1               5                   10
```

<210> SEQ ID NO 22
<211> LENGTH: 11
<212> TYPE: PRT
<213> ORGANISM: Homo sapiens

<400> SEQUENCE: 22

```
Ala Cys Asp Gln Arg Val Leu Ile Val Arg Arg
1               5                   10
```

<210> SEQ ID NO 23
<211> LENGTH: 10
<212> TYPE: PRT
<213> ORGANISM: Homo sapiens

<400> SEQUENCE: 23

```
Leu Trp Asp Val Pro Ser Trp Leu Glu Arg
1               5                   10
```

<210> SEQ ID NO 24
<211> LENGTH: 10
<212> TYPE: PRT
<213> ORGANISM: Homo sapiens

<400> SEQUENCE: 24

```
Ala Ile Ser Gln Asp Thr Thr Val Gly Arg
1               5                   10
```

<210> SEQ ID NO 25
<211> LENGTH: 11
<212> TYPE: PRT
<213> ORGANISM: Homo sapiens

<400> SEQUENCE: 25

```
Ala Ala Cys Asp Gln Arg Val Leu Ile Val Arg
1               5                   10
```

<210> SEQ ID NO 26
<211> LENGTH: 9
<212> TYPE: PRT
<213> ORGANISM: Homo sapiens

<400> SEQUENCE: 26

```
Asp Gln Arg Val Leu Ile Val Arg Arg
1               5
```

<210> SEQ ID NO 27
<211> LENGTH: 11
<212> TYPE: PRT
<213> ORGANISM: Homo sapiens

<400> SEQUENCE: 27

```
Ile Val Arg Arg Asn Leu Leu Asp Leu Ser Lys
1               5                   10
```

<210> SEQ ID NO 28
<211> LENGTH: 11
<212> TYPE: PRT
<213> ORGANISM: Homo sapiens

<400> SEQUENCE: 28

```
Leu Ser Lys Glu Glu Lys Asn His Phe Val Arg
```

-continued

```
<210> SEQ ID NO 29
<211> LENGTH: 7
<212> TYPE: DNA
<213> ORGANISM: Homo sapiens

<400> SEQUENCE: 29 gagatga                                                            7

<210> SEQ ID NO 30
<211> LENGTH: 7
<212> TYPE: DNA
<213> ORGANISM: Homo sapiens

<400> SEQUENCE: 30 gacatgt                                                            7

<210> SEQ ID NO 31
<211> LENGTH: 9
<212> TYPE: PRT
<213> ORGANISM: Homo sapiens

<400> SEQUENCE: 31

Ile Ser Gln Asp Thr Thr Val Gly Arg
1               5

<210> SEQ ID NO 32
<211> LENGTH: 9
<212> TYPE: PRT
<213> ORGANISM: Homo sapiens

<400> SEQUENCE: 32

Ala Gly Glu Glu Leu Pro Val Thr Arg
1               5

<210> SEQ ID NO 33
<211> LENGTH: 10
<212> TYPE: PRT
<213> ORGANISM: Homo sapiens

<400> SEQUENCE: 33

Met Ser Leu Gln Arg Gln Phe Leu Arg Thr
1               5                   10

<210> SEQ ID NO 34
<211> LENGTH: 9
<212> TYPE: PRT
<213> ORGANISM: Homo sapiens

<400> SEQUENCE: 34

Ser Leu Gln Arg Gln Phe Leu Arg Thr
1               5

<210> SEQ ID NO 35
<211> LENGTH: 9
<212> TYPE: PRT
<213> ORGANISM: Homo sapiens

<400> SEQUENCE: 35

Met Ala Leu Gln Arg Gln Phe Leu Arg
1               5

<210> SEQ ID NO 36
```

```
<211> LENGTH: 9
<212> TYPE: PRT
<213> ORGANISM: Homo sapiens

<400> SEQUENCE: 36

Met Leu Leu Gln Arg Gln Phe Leu Arg
1               5

<210> SEQ ID NO 37
<211> LENGTH: 9
<212> TYPE: PRT
<213> ORGANISM: Homo sapiens

<400> SEQUENCE: 37

Met Arg Leu Gln Arg Gln Phe Leu Arg
1               5

<210> SEQ ID NO 38
<211> LENGTH: 9
<212> TYPE: PRT
<213> ORGANISM: Homo sapiens

<400> SEQUENCE: 38

Met Ser Leu Gln Arg Leu Phe Leu Arg
1               5

<210> SEQ ID NO 39
<211> LENGTH: 9
<212> TYPE: PRT
<213> ORGANISM: Homo sapiens

<400> SEQUENCE: 39

Met Ser Leu Gln Arg Gln Phe Leu Glu
1               5

<210> SEQ ID NO 40
<211> LENGTH: 9
<212> TYPE: PRT
<213> ORGANISM: Homo sapiens

<400> SEQUENCE: 40

Met Ser Leu Gln Arg Gln Phe Leu Lys
1               5

<210> SEQ ID NO 41
<211> LENGTH: 9
<212> TYPE: PRT
<213> ORGANISM: Homo sapiens

<400> SEQUENCE: 41

Ile Ser Leu Gln Arg Gln Phe Leu Arg
1               5

<210> SEQ ID NO 42
<211> LENGTH: 32
<212> TYPE: DNA
<213> ORGANISM: Homo sapiens

<400> SEQUENCE: 42
agaatgagtg ctcctaaact cctctctctg gg                          32

<210> SEQ ID NO 43
<211> LENGTH: 24
<212> TYPE: DNA
<213> ORGANISM: Homo sapiens
```

-continued

```
<400> SEQUENCE: 43
catgtgagaa aagctggtcc ctca                                              24

<210> SEQ ID NO 44
<211> LENGTH: 24
<212> TYPE: DNA
<213> ORGANISM: Homo sapiens

<400> SEQUENCE: 44
tggatatggc aaagcgcaca actc                                              24

<210> SEQ ID NO 45
<211> LENGTH: 30
<212> TYPE: DNA
<213> ORGANISM: Homo sapiens

<400> SEQUENCE: 45
taaatggaaa tgttctcaaa ttgtggcgtg                                        30

<210> SEQ ID NO 46
<211> LENGTH: 8
<212> TYPE: PRT
<213> ORGANISM: Homo sapiens

<400> SEQUENCE: 46

Ser Val Val Glu Phe Ser Ser Leu
1               5
```